United States Patent [19]
Habuchi et al.

[11] Patent Number: 5,827,713
[45] Date of Patent: Oct. 27, 1998

[54] DNA CODING FOR SULFOTRANSFERASE

[75] Inventors: Osami Habuchi, Nagoya; Masakazu Fukuta, Mie-ken, both of Japan

[73] Assignee: Seikagaku Kogyo Kabushiki Kaisha, Tokyo, Japan

[21] Appl. No.: 655,878

[22] Filed: May 31, 1996

[30] Foreign Application Priority Data

May 31, 1995 [JP] Japan ..................................... 7-134358

[51] Int. Cl.⁶ .............................. C12N 9/10; C12N 1/20; C12N 5/00; C07H 21/04
[52] U.S. Cl. ................... 435/193; 435/252.3; 435/320.1; 435/325; 536/23.2; 935/22
[58] Field of Search ................................. 435/193, 320.1, 435/252.3, 325; 536/23.2, 23.5; 935/22

[56] References Cited

PUBLICATIONS

"Current Protocols in Molecular Biology." Ausubel, F.M. (Ed.), Wiley & Sons, New York, USA, vol. 1, 1987, pp. 6.4.1–6.4.10.

Rudinger, J. (1976) Characteristics of the amino acids as components of a peptide hormone sequence, In Peptide Hormones, Ed. J. A. Parsons, pp. 1–7, Jun. 1976.

Fukuta et al. 1995 Molecular Cloning and Expression of Chick Chondrocyte Chondroitin 6–Sulfotransferase, J. Biol. Chem. 270 (31): 18575–18580, Aug. 4, 1995.

Sugumaran et al. (1995) Purification, Photoaffinity Labeling, and Characterization of a Single Enzyme for 6–Sulfation of both Chondroitin Sulfate and Keratan Sulfate, J. Biol. Chem. 270 (38): 22483–22487, Sep. 22, 1995.

Habuchi et al. (1993) Purification of Chondroitin 6–Sulfotransferase Secreted from Cultured Chick Embryo Chondrocytes, J. Biol. Chem. 268 (29): 21968–21974, Oct. 15, 1993.

Habuchi and Miyashita (1982) Separation and Characterization of Chondroitin 6–Sulfotransferase and Chondroitin 4–Sulfotransferase from Chick Embryo Cartilage, Biochimica et Biophysica Acta 717: 414–421, Aug. 1982.

*Primary Examiner*—Robert A. Wax
*Assistant Examiner*—Einar Stole
*Attorney, Agent, or Firm*—Knobbe, Martens, Olson & Bear, LLP

[57] ABSTRACT

Chondrotin 6-sulfotransferase (C6ST), for transferring sulfate group to the hydroxyl group at C-6 position of N-acetylgalactosamine residue or galactose residue of glycosaminoglycan, was purified from a culture liquid of chick embryo chondrocytes to determine its partial amino acid sequences. Partial cDNA of C6ST was amplified from poly(A)₊prepared from the chondrocytes, by means of PCR by using oligonucleotide primers prepared on the basis of the determined sequences. Entire length cDNA of C6ST was obtained from a cDNA library by means of hybridization by using an obtained cDNA fragment as a probe.

15 Claims, 5 Drawing Sheets

```
Peptide 1                   Glu Lys Glu Asn Asn Phe Ile
Primer 1s    5'  CA AAGCTT GAA AAA GAA AAT AAT TTT AT   3'
                    |_____|  G   G   G   C   C   C
                    HindIII Peptide 1        Arg Val Ser Asp Lys Leu Lys
Primer 2s    5'  CGG GTG TCG GAT AAA CTT AA       3'
                 A T   T  AGT  C   G   C
                                       A
                                       G Peptide 2        Phe Ile Ser Pro Ala Pro Glu
Primer 3a    3'  AAA TAG AGG GGG CGG GGG CTT CTTAAG CT   5'
                  G   T  TCT  T   T   T      |_____|
                      A                       EcoRI
```

DNA CODING FOR SULFOTRANSFERASE

BACKAROUND OF THE INVENTION

1. Field of the Invention

The present invention relates to novel DNA coding for sulfotransferase, a novel polypeptide expressed from a DNA fragment originating from the DNA, and an antibody reactive with the polypeptide.

2. Prior Art

Chondroitin sulfate is a representative sulfated mucopolysaccharide (glycosaminoglycan). Chondroitin sulfate proteoglycan (CSPG) exists abundantly in cartilage, and is considered to participate in expression and maintenance of the phenotype of chondrocyte (Tsukahara, T., Okamura, M., Suzuki, S., Iwata, H., Miura, T., and Kimata, K. (1991) *J. Cell Sci.* 100, 387–395). CSPG also exists in various tissues other than cartilage, and is considered to play an important role for intercellular interactions (Kjellen, L. and Lindahl, U. (1991) *Annu. Rev. Biochem.* 60, 443–475).

Major chondroitin sulfate found in tissues of mammalian and avian has sulfate groups at C-6 or C-4 positions of acetylgalactosamine residues. The following knowledge has been obtained for the ratio of 6-sulfation/4-sulfation. (i) The ratio of chondroitin 6-sulfate/chondroitin 4-sulfate (6/4 ratio) increases along with progress of final differentiation of carilage. (ii) The 6/4 ratio in CSPG decreases in skin of rat along with passage of days after the birth. (iii) As a result of comparison between two types of arterial smooth muscle cells obtained from atherosclerosis-resistant and sensitive varieties of pigeon, the major component is chondroitin 4-sulfate in the resistant variety in relation to both of CSPG and DSPG (dermatan sulfate proteoglycan), however, the major component is chondroitin 6-sulfate in the sensitive variety. (iv) When the culture condition is changed in monocytic leukemia cells (M1) such that the culture condition is directed to cell proliferation, inhibition of proliferation at a high density, and occurrence of induction of differentiation to macrophage, then the 6/4 ratio in CSPG decreases a s the condition changes in an order of proliferation, inhibition of proliferation, and induction of differentiation, and chondroitin 4-sulfate is almost totally synthesized in a state of induction of differentiation. (v) As a result of comparison between human colon normal tissue and human colon tumor tissue, chondroitin 6-sulfate and chondroitin increase in PG in the tumor tissue as compared with the normal tissue. (vi) As a result of comparison between those before and after calcification in mouse osteoblast, the 6/4 ratio of DSPG decreases after calcification as compared with that before calcification. (vii) When PDGF (platelet derived growth factor) is added to a culture medium of monkey arterial smooth muscle cells, the 6/4 ratio in versican-like CSPG increases as compared with a control with no addition of PDGF (Glycobiology Series (I), "Diversified World of Saccharides", Kodansha, pp. 164, 166).

It has been also reported for chondroitin sulfate that two sulfate groups exist per one repeating disaccharide unit. For example, GlcAβ1→3GalNAc(4,6-bisS) has been found in subcultured chick embryo chondrocytes, mouse mast cells differentiated from myeloid cells obtained by cultivation in a conditioned medium-added medium obtained by cultivating mouse spleen cells, rat glomeruli, culture liquid of organotypic human colonic mucosa, rat serosa mast cells, secretory granules of human lung mast cells, human monocyte and macrophage originating from monocyte activated by phorbol myristate acetate, mouse osteoblast, rat glomerulus vascular membrane cells, and sea-cucumber body wall. In addition, GalNAc(4,6-bisS) has been found in the nonreducing terminal of the chondroitin sulfate from chick embryo epiphyseal cartilage, rat processus xiphoideus cartilage, and cell layer obtained by cultivating chick embryo chondrocyte. Further, GalNAc(4,6-bisS) β1→4GlcAβ1→3GalNAc (4,6-bisS) has been found in the nonreducing terminal of the chondroitin sulfate from thrombomodulin extracted and purified from rabbit lung. Moreover, GlcA(2S)-GalNAc(6S) has been found in the nonreducing terminal of the chondroitin sulfate from mast cells originating from mouse lymph node (Glycobiology Series (I), "Diversified World of Saccharides", Kodansha, p. 166).

It is considered that the diversification of the sulfation pattern of chondroitin sulfate as described above reflects a molecular basis of the function of chondroitin sulfate. It is also considered that sulfation plays an important role in expression of physiological activities of chondroitin sulfate. Considering the importance of sulfation in expression of physiological activities of chondroitin sulfate, it is assumed that a method for sulfating a specific site of chondroitin sulfate is indispensable to analyze physiological activities of chondroitin sulfate and modify its function. Sulfation at a specific site of a sugar residue of glycosaminoglycan is catalyzed by a sulfotransferase specific to the site.

If a gene of sulfotransferase for glycosaminoglycan is cloned, information on substrate specificity concerning the acceptor may be obtained, providing an approach useful to study the relationship between structure and function of glycosaminoglycan. It is assumed that various types of glycosaminoglycan sulfotransferase participate in synthesis of glycosaminoglycan. However, cloning of cDNA of sulfotransferase is difficult. In fact, those having been cloned only include cDNA's of N-sulfotransferase/N-deacetylase from rat liver, heparin-producing cell line, and mouse mast cell tumor.

The present inventors have apparently homogeneously purified, from a culture supernatant of chick chondrocytes cultured in a serum-free medium, chondroitin 6-sulfotransferase (hereinafter abbreviated as "C6ST", if necessary) which transfers sulfate group from 3'-phosphoadenosine 5'-phosphosulfate to the hydroxyl group at C-6 position of N-acetylgalactosamine residue of glycosaminoglycan such as chondroitin (Habuchi, O., Matsui, Y., Kotoya, Y., Aoyama, Y., Yasuda, Y., and Noda, M. (1993) *J. Biol. Chem.* 268, 21968–21974). However, the yield of the enzyme was low, namely it was 0.015% with respect to an amount of total proteins in the culture supernatant. Therefore, it has been difficult to obtain the enzyme in an industrially usable amount. In addition, it has been impossible to prepare an antibody against the enzyme for immunologically detecting the enzyme, because the enzyme protein (or any peptide originating from the enzyme protein) as an antigen has not been obtained in a satisfactory amount.

Usually, in order to obtain a large amount of a protein which is difficult to be obtained from a natural source, it is useful to clone a gene coding for the protein in accordance with a genetic engineering technique. For this purpose, it is indispensable to determine an amino acid sequence of the protein. However, the chondroitin 6-sulfotransferase described above had a molecular weight of 75,000 on SDS-PAGE. The molecular weight was not small at all. Further, the chondroitin 6-sulfotransferase was obtained in a low yield. As a result, it has not been achieved to determine an amino acid sequence, making it difficult to clone a gene coding for the enzyme.

Considering the importance of sulfation in expression of physiological activities of chondroitin sulfate, the enzyme, which transfers sulfate group to chondroitin sulfate, is extremely important not only to perform a study on analysis of function of chondroitin sulfate but also to provide a certain type of chondroitin sulfate in order to create pharmaceuticals having physiological activities preferred for human. In particular, chondroitin 6-sulfotransferase (C6ST), which transfers sulfate group from 3'-phosphoadenosine 5'-phosphosulfate to the hydroxyl group at C-6 position of N-acetylgalactosamine residue of chondroitin, has been purified. Now it is desired to clone cDNA which is necessary to mass-produce this enzyme to such a degree that this enzyme can be industrially used. It is also desired to prepare an antibody against this protein, which is necessary to immunologically detect this enzyme. It is further desired to mass-produce an antigen which is necessary to prepare the antibody.

SUMMARY OF THE INVENTION

The present invention has been made taking the aforementioned viewpoints into consideration, an object of which is to provide DNA coding for chondroitin 6-sulfotransferase which transfers sulfate group to the hydroxyl group at C-6 position of N-acetylgalactosamine residue of chondroitin, a polypeptide expressed from a DNA fragment originating from the DNA, and an antibody which is reactive with the polypeptide.

The present inventors have diligently searched for DNA coding for chondroitin 6-sulfotransferase which is an enzyme to selectively transfer sulfate group to the hydroxyl group at C-6 position of N-acetylgalactosamine residue contained in chondroitin and chondroitin sulfate, succeeded in cloning of cDNA coding for the enzyme, and confirmed expression of chondroitin 6-sulfotransferase by using the cDNA. Thus the present inventors have achieved the present invention.

Further, the present inventors have prepared a novel peptide from a DNA fragment originating from cDNA coding for the enzyme, and confirmed that an antibody obtained by using the peptide as an antigen is reactive with the peptide and C6ST. Thus the present inventors have achieved the present invention.

Namely, the present invention lies in DNA coding for a sulfotransferase having the following properties:

(i) action: sulfate group is transferred from a sulfate group donor to the hydroxyl group at C-6 position of N-acetylgalactosamine residue or galactose residue of glycosaminoglycan;

(ii) substrate specificity: sulfate group is transferred to chondroitin, chondroitin sulfate originating from chick embryo cartilage, chondroitin sulfate A, chondroitin sulfate C, and keratan sulfate originating from cornea, but no sulfate group is substantially transferred to chondroitin sulfate E, dermatan sulfate, and heparan sulfate;

(iii) optimum reaction pH: about 6.4;

(iv) inhibition and activation: the activty of this enzyme is increased by protamine and $MnCl_2$; and (v) molecular weight: this enzyme has a molecular weight of about 75,000 estimated by SDS-polyacrylamide gel electrophoresis under a reduced condition, while it has a molecular weight of about 160,000 estimated by gel filtration under a non-reduced condition.

In another aspect, the present invention lies in DNA coding for at least a part of a sulfotransferase having an amino acid sequence shown in SEQ ID NO: 2, with or without substitution, deletion, or insertion of one or more amino acid residues or any combination thereof which do not substantially deteriorate an activity to transfer sulfate group from a sulfate group donor to the hydroxyl group at C-6 position of N-acetylgalactosamine residue or galactose residue of glycosaminoglycan.

The DNA of the present invention specifically includes DNA having a base sequence coding for an amino acid sequence represented by amino acid numbers of −33 to 425 in SEQ ID NO: 2, DNA having a base sequence coding for an amino acid sequence represented by amino acid numbers of −14 to 425 in SEQ ID NO: 2, DNA having a base sequence coding for an amino acid sequence represented by amino acid numbers of 1 to 425 in SEQ ID NO: 2, and DNA having a base sequence coding for an amino acid sequence represented by amino acid numbers of 5 to 154 in SEQ ID NO: 2.

In still another aspect of the present invention, there is provided a partial peptide of the sulfotransferase encoded by the aforementioned DNA. The partial peptide specifically includes a peptide having an amino acid sequence represented by amino acid numbers 5 to 154 in SEQ ID NO: 2.

In still another aspect of the present invention, there is provided an antibody reactive with a sulfotransferase having an amino acid sequence shown in SEQ ID NO: 2 or a partial peptide thereof.

The enzyme encoded by the DNA of the present invention is conveniently called "condroitin 6-sulfotransferase". However, these terms do not mean that the substrate for the enzyme is limited to chondroitin. The enzyme of the present invention has the activity to transfer sulfate group not only to chondroitin, but also to chondroitin sulfate originating from chick embryo cartilage, chondroitin sulfate A, chondroitin sulfate C, and keratan sulfate originating from cornea by adding protamine or the like.

The present invention will be explained in detail below.

<1>DNA Coding For Chondroitin 6-Sulfotransferase Of The Present Invention

The chondroitin 6-sulfotransferase encoded by the DNA of the present invention is an enzyme which has been purified by the present inventors from a culture supernatant of chick chondrocytes cultured in a serum-free medium (Habuchi, O., Matsui, Y., Kotoya, Y., Aoyama, Y., Yasuda, Y., and Noda, M. (1993) *J. Biol. Chem.* 268, 21968–21974), and which has the following enzymatic properties:

(i) action: sulfate group is transferred from a sulfate group donor to the hydroxyl group at C-6 position of N-acetylgalactosamine residue or galactose residue of glycosaminoglycan;

(ii) substrate specificity: sulfate group is transferred to chondroitin, chondroitin sulfate originating from chick embryo cartilage, chondroitin sulfate A, and chondroitin sulfate C, but no sulfate group is substantially transferred to chondroitin sulfate E, dermatan sulfate, and heparan sulfate, while;

sulfate group is also transferred to keratan sulfate originating from cornea, and it has been confirmed by the present inventors that the site of transfer is hydroxyl group at C-6 position of galactose residue;

(iii) optimum reaction pH: about 6.4;

(iv) inhibition and activation: the activty of this enzyme is increased by protamine and $MnCl_2$; and (v) molecular weight: the enzyme has a molecular weight of about 75,000 estimated by SDS (sodium dodecyl sulfate) -polyacrylamide gel electrophoresis (SDS-PAGE) under a reduced condition, while it has a molecular weight of about 160,000 estimated by gel filtration (Superose 12, produced by Pharmacia LKB Biotechnology) under a non-reduced condition.

The DNA of the present invention is DNA having been isolated for the first time in accordance with the present invention, which codes for the chondroitin 6-sulfotransferase. The base sequence of the DNA of the present invention is not specifically limited provided that it codes for the chondroitin 6-sulfotransferase. However, the base sequence specifically includes a base sequence capable of coding for an amino acid sequence shown in SEQ ID NO: 2. More specifically, the base sequence of the DNA of the present invention includes a base sequence shown in SEQ ID NO: 1. However, those skilled in the art will readily understand that DNA's having different base sequences due to degeneracy of genetic codes are also included in the DNA of the present invention.

The DNA of the present invention may have, in the amino acid sequence described above, substitution, deletion, insertion, or rearrangement of one or more amino acid residues or any combination thereof which does not substantially deteriorate the activity to transfer sulfate group from a sulfate group donor to the hydroxyl group at C-6 position of N-acetylgalactosamine residue or galactose residue of glycosaminoglycan. Any of such DNA's is included in the DNA of the present invention.

The DNA of the present invention may be a single strand comprising only a coding strand which codes for C6ST, or it may be a double strand comprising the single strand and a DNA strand having a sequence complementary thereto.

The DNA of the present invention may have an entire length of a coding region which codes for the entire C6ST, or it may be a fragment which codes for a partial peptide of C6ST.

In the present invention, the DNA has been obtained for the first time, as mentioned in examples described later on, by means of cDNA cloning comprising the steps of (i) determining a partial amino acid sequence of C6ST, (ii) preparing an oligonucleotide probe for PCR on the basis of the amino acid sequence, (iii) amplifying partial cDNA of C6ST from poly(A)$^+$ RNA originating from chick embryo chondrocyte in accordance with the PCR method, and (iv) selecting entire length cDNA of C6ST from a cDNA library originating from chick embryo chondrocyte. Since the amino acid sequence coding by the DNA of the present invention has been clarified by the present invention, the DNA can be synthesized on the basis of the sequence.

A method for obtaining the DNA of the present invention will be specifically explained below.

(1) Determination Of Partial Amino Acid Sequence Of Chondroitin 6-Sulfotransferase (C6ST) And Preparation Of Primers For PCR (i) Purification of C6ST The chondroitin 6-sulfotransferase can be purified from cultured cells such as chondrocytes which express the chondroitin 6-sulfotransferase by combining ordinary purification methods for proteins and ordinary purification methods for sulfotransferases. Specifically, purification is preferably performed in accordance with a method described in *J. Biol. Chem.* 268, (29), 21968–21974 (1993). Namely, substantially homogeneous C6ST is obtained, for example, from a culture supernatant of chick embryo chondrocytes cultured in a serum-free medium by means of affinity chromatography by using Heparin-Sepharose CL6B (available from Pharmacia LKB Biotechnology), wheat germ agglutinin-agarose (available from Seikagaku Corp.), and 3',5'-ADP-agarose (available from Sigma). A method for measuring the sulfotransferase activity and a method for determining the position of sulfate group transfer will be described in detail in examples.

(ii) Determination of partial amino acid sequence of chondroitin 6-sulfotransferase It is known that a sugar chain is connected to purified C6ST. Accordingly, in order to remove the sugar chain, purified C6ST is digested with a sugar chain-degrading enzyme such as N-glycanase. C6ST having been deglycosylated as described above is subjected to, for example, SDS-PAGE (SDS-polyacrylamide gel electrophoresis), and thus it is separated, followed by transfer onto, for example, a polyvinylidene fluoride (PVDF) membrane or a nitrocellulose membrane. The membrane is stained with a dye for staining proteins, such as Coomassie Brilliant Blue or Amido Black. A protein band formed after the digestion with N-glycanase is excised, and it is used for determining an amino acid sequence of deglycosylated C6ST. In case of the determination of an internal amino acid sequence of C6ST is necessary, deglycosylated C6ST is subjected to SDS-PAGE or the like, and thus it is separated. The gel is stained with a dye for staining proteins, such as Coomassie Brilliant Blue or Amido Black. A protein band formed after the digestion with N-glycanase is excised, and it is used for fragmentation.

The method for fragmentation is not specifically limited. However, it is preferable to use a proteolytic enzyme such as protease V8 (sequencing grade, produced by Boehringer Mannheim). Alternatively, the excised gel may be allowed to contact with the proteolytic enzyme, followed by separation by means of SDS-PAGE or the like. A convenient operation may be used, which is based on a method of Cleveland, D. W., Fischer, S. G., Kirshner, M. W., and Laemmli, U. K. (1977) *J. Biol. Chem.* 252, 1102–1106. Namely, this method comprises the steps of excising a protein band, inserting it into a well in another gel, placing a buffer containing a proteolytic enzyme on the inserted gel to perform SDS-PAGE, temporarily stopping electrophoresis by turning-off the power source before a forward end of a dye enters a separating gel, performing enzymatic digestion for about 30 minutes, and then starting electrophoresis again. According to this method, the enzymatic digestion and the separation of peptide fragments after the digestion can be performed in accordance with the one-step operation, which is convenient. Peptides formed by the protease digestion are transferred, for example, onto a PVDF membrane or a nitrocellulose membrane. The membrane is stained with a dye for staining proteins, such as Coomassie Brilliant Blue or Amido Black. After that, peptide bands are excised. The PVDF membrane or the nitrocellulose membrane containing the peptides generated after the digestion with the proteolytic enzyme can be used to determine amino terminal sequences of the peptides in accordance with a known method. Alternatively, the amino acid sequence can be determined in accordance with the aforementioned method by entrusting a reliable third party with the sequencing task.

Examples of partial amino acid sequences determined as described above are shown in SEQ ID NOs: 3 to 6.

(iii) Synthesis of oligonucleotide primers

Once the partial amino acid sequence of C6ST is determined, oligonucleotide primers for PCR can be prepared on the basis of the amino acid sequence. It is preferable to use a region in the amino acid sequence having degeneracy as less as possible. Examples of such primers are shown in SEQ ID NOs: 7 and 8 as sense primers, and in SEQ ID NO: 9 as an antisense primer. The primer shown in SEQ ID NO: 7 has a sequence containing a HindIII site at its 5'-terminal. The antisense primer shown in SEQ ID NO: 9 has a sequence containing an EcoRI site at its 5'-terminal. These arrangements are provided for convenient operation to insert a DNA fragment amplified by PCR into a vector.

(2) Preparation Of Partial cDNA of C6ST (i) Preparation of poly(A)$^+$RNA containing mRNA coding for C6ST (ii) Preparation of total RNA Total RNA can be obtained in accordance with a known method (for example, Kingston, R. E., (1991) in *Current Protocols in Molecular Biology*, Suppl. 14, Unit 4.2, Greene Publishing Associates and Wiley Interscience, New York). The material for total RNA preparation is not limited provided that mRNA of the chondroitin 6-sulfotransferase is expressed in the material. However, cell lines are preferred because they are easily handled and capable of proliferation. Among the cell lines, chick embryo chondrocytes are especially preferred. The chondrocytes can be cultured in accordance with a known method (for example, Kim, J. J. and Conrad, H. E. (1976) *J. Biol. Chem.* 251, 6210–6217; Kim, J. J. and Conrad, H. E. (1977) *J. Biol. Chem.* 252, 8292–8299; Kim, J. J. and Conrad, H. E. (1980) *J. Biol. Chem.* 255, 1586–1597). The medium is not specifically limited provided that the cell lines can grow in the medium. However, Dulbecco's Modified Eagle's medium or the like is preferred because it is well used in ordinary culture, it is easily available, and it allows the cell lines to grow therein. The medium is preferably adjusted to have a pH in a neutral region, especially at pH 7.0. D-Glucose is preferably added to the medium in an amount of about 2 g/l. In order to avoid growth of microorganisms, antibiotics such as penicillin and streptomycin are preferably added to the medium. Fetal bovine serum is preferably added to the medium in an amount of 10%.

The cells may be cultured in the same manner as in ordinary cell lines by using the medium as described above and using roller bottles or dishes. The cells are preferably cultured in a carbon dioxide gas incubator. The concentration of carbon dioxide gas is preferably adjusted at 3 to 7%, and air is preferably adjusted at 97 to 93% in the incubator. The temperature is preferably adjusted at about 37° to 38° C.

Total RNA can be obtained from the cells cultured as described above in accordance with a method ordinarily used for preparing total RNA. However, total RNA is preferably prepared in accordance with a guanidine thiocyanate/CsCl method (Kingston, R. E., (1991) in *Current Protocols in Molecular Biology*, Suppl. 14, Unit 4.2, Greene Publishing Associates and Wiley Interscience, New York).

(i-ii) Preparation of poly(A)$^+$RNA

Poly(A)$^+$RNA can be purified from the total RNA obtained as described above by means of, for example, oligo-(dT) cellulose column chromatography.

(i-iii) Amplification of partial cDNA of C6ST by PCR method

Partial cDNA of C6ST can be amplified in accordance with reverse transcription PCR (polymerase chain reaction) by using the poly(A)$^+$RNA as a template and using the oligonucleotide primers. PCR may be performed in the same manner as in an ordinary method, however, it may be performed in accordance with the following specified method. A buffer (final volume 20 μl) containing the poly (A)$^+$RNA (1 μg), oligonucleotide 3a (50 pmol), four species of deoxynucleoside triphosphates (each 500 μM), M-MLV reverse transcriptase (200 units, produced by Gibco BRL), dithiothreitol (1 mM), and RNase inhibitor (120 units, produced by Takara Shuzo) is incubated at 37° C. for 60 minutes to synthesize cDNA primary strand. After that, a reaction solution (final volume 100 μl) containing the reverse transcription reaction mixture described above (10 μl), the oligonucleotide primers (50 pmol of each of the sense and antisense primers), four species of deoxynucleoside triphosphate (each 100 μM), and Taq polymerase (2.5 units) is subjected to 30 cycles of a repeating reaction cycle composed of periods at 94° C. for 1 minute, 45° C. for 1 minute, and 55° C. for 3 minutes.

Partial cDNA thus obtained is used as a hybridization probe for screening entire length cDNA (cDNA containing entire length of a coding region) from a cDNA library.

(3) Preparation of cDNA library (i) Synthesis of cDNA and preparation of recombinant DNA cDNA can be synthesized by means of a reverse transcriptase reaction by using the poly(A)$^+$RNA as a template. It is convenient to use a commercially available kit for cDNA synthesis. For example, when TimeSaver cDNA synthesis kit (Pharmacia LKB Biotechnology) is used, it is possible to synthesize cDNA, and ligate the CDNA with a cloning vector (for example, λgt11 digested with EcoRI). It is also preferable in the present invention to use λgt11 digested with EcoRI. As for the primer for the reverse transcriptase reaction, it is preferable to use random oligonucleotide primers. Recombinant DNA, which is obtained by ligating the cDNA with the cloning vector, is introduced (subjected to transfection) into cells of a host bacterium. It is necessary to select the cells of the host bacterium to be used, depending on the cloning vector to be used. However, in an ordinary case, a combination of *Escherichia coli* (*E. coli*) and a cloning vector to use *E. coli* as a host is often used.

The transfection is usually performed by mixing recombinant DNA with *E. coli* in which permeability of cell membrane has been changed in the presence of 30 mM calcium chloride. In the case of a λ phage vector such as λgt11, recombinant DNA can be directly introduced into calcium chloride-treated *E. coli*. However, a method is generally used in which recombinant DNA is previously encapsulated into outer coat of the phage in vitro (referred to as "in vitro packaging") so that *E. coli* is efficiently infected therewith. A kit for this purpose is also commercially available (for example, Gigapack II packaging extract, produced by Stratagene). It is also preferable in the present invention to use this method.

Recombinant DNA subjected to the in vitro packaging is transfected to *E. coli*. However, it is necessary to select an *E. coli* strain depending on a cloning vector to be used. Namely, when a cloning vector containing an antibiotic resistance gene is used, *E. coli* should not have a property of resistance to a corresponding antibiotic. When a cloning vector containing a gene such as β-galactosidase gene (lacZ) is used, it is necessary to select an *E. coli* strain which expresses no β-galactosidase activity. The fact described above is necessary to screen *E. coli* transfected with the recombinant DNA. For example, when λgt11 is used as the cloning vector, it is adequate to select an *E. coli* strain such as *E. coli* Y1088 which expresses no β-galactosidase activity. *E. coli*, into which the recombinant vector has been introduced, can be screened on the basis of acquired resistance to antibiotic and acquired β-galactosidase activity. Specifically, cells of *E. coli* are plated on an agar medium, and grown colonies may be selected. The grown colonies of *E. coli* (*E. coli* transfected with the recombinant DNA) constitute a cDNA library. When λgt11 is used as the vector, it may be suspended in a soft agar medium together with indicator bacterial cells, and the suspension may be layered on an agar medium to form plaques. Phage plaques harboring the vector with the inserted DNA fragment express no λ-galactosidase activity, and hence they can be easily selected.

(ii) Cloning of entire length cDNA of C6ST

Next, a phage clone having entire length cDNA of C6ST can be selected from the cDNA library obtained as described above by means of hybridization by using the partial cDNA of C6ST as a probe. The hybridization may be performed in accordance with an ordinary method.

Phage DNA is prepared from a selected positive clone, and is digested with an appropriate restriction enzyme. Thus C6ST cDNA can be excised. Obtained cDNA is used as it is, or after subcloned into an appropriate plasmid to determine a base sequence.

The base sequence of C6ST cDNA determined as described above and an amino acid sequence deduced from the base sequence are shown in SEQ ID NO: 1. Only the amino acid sequence is shown in SEQ ID NO: 2. Two in-frame ATG codons are contained in a 5'-terminal portion of an open reading frame of C6ST cDNA. In a base sequence around the first ATG codon, purine at a position of −3 is not conserved, but G (guanine) at a position of +4 is conserved as compared with the consensus sequence at the translation initiation region of eucaryotic cells. This fact satisfies the finding of Kozak that G at the position of +4 is essential for efficient translation when no purine exists at the position of −3 (Kozak, M. (1986) *Cell,* 44, 283–292). In a base sequence around the second ATG codon, the position of −3 is A (adenine), and the position of +4 is not G but A. This fact also partially conforms to the consensus sequence. Accordingly, any of the ATG codons has the possibility to function as an initiation codon.

It is known that β-1,4-galactosyltransferase contains two ATG codons in its frame (Nakazawa, K. et al. (1988) *J. Biochem.,* 104, 165–168; Shaper, N. et al. (1988) *J. Biol. Chem.,* 263, 10420–10428). In addition, Shaper et al. have demonstrated that β-1,4-galactosyltransferase is synthesized in both long and short forms as a result of initiation of translation from the two positions. Further, Lopez et al. have demonstrated an evidence which suggests that the long form preferentially targets plasma membrane, while the short form primarily exists in Golgi body (Lopez, L. et al. (1991) *J. Biol. Chem.,* 266, 15984–15991). In the same manner as described above, C6ST also has the possibility that the both of the two ATG codons function as initiation codons. However, this speculation is not clear.

A single open reading frame starting from the first ATG codon allows suggestion of a protein composed of 458 amino acid residues with a molecular weight of 52,193 and having six sites which possibly serve as N-binding glycosylation sites. A hydropathy plot (FIG. 4) prepared from the amino acid sequence allows recognition of one conspicuous hydrophobic portion having a length of 14 residues ranging from 24th to 37th amino acid residues as counted from the N-terminal, suggesting that the protein has a transmembrane domain.

The DNA obtained as described above may have substitution, deletion, or insertion of one or more nucleotides of any combination thereof to cause substitution, deletion, or insertion of one or more amino acid residues or any combination thereof provided that C6ST encoded by the DNA is not substantially deteriorated for its activity to transfer sulfate group from a sulfate group donor to the hydroxyl group at C-6 position of N-acetylgalactosamine residue or galactose residue of glycosaminoglycan. The substitution, deletion, or insertion of one or more nucleotides can be introduced into the DNA sequence by synthesizing a sequence which has restriction enzyme cleavage terminals at both ends and contains both side portions of a mutation point, and replacing a corresponding portion of the non-mutated DNA sequence with the synthesized sequence. Alternatively, the substitution, insertion, or deletion can be also introduced into the DNA sequence in accordance with a method such as a site-specific mutagenesis method (Kramer, W. and Frits, H. J., *Meth. in Enzymol.,* 154, 350 (1987); Kunkel, T. A. et al., *Meth. in Enzymol.,* 154, 367 (1987)).

<2>Utilization Of DNA Coding For C6ST Of The Present Invention

C6ST can be produced by culturing, in an appropriate medium, cells harboring the DNA of the present invention, to produce and accumulate C6ST in the medium, and collecting C6ST from the medium. In order to express the DNA of the present invention, it is possible to use a host-vector system usually used for producing proteins. However, mammalian cells such as COS-7 cells are preferred. As for the expression, the DNA of the present invention may be directly expressed, or it may be expressed as a fusion protein containing another protein. The DNA of the present invention may be expressed in its entire length, or a part of it may be expressed as a partial peptide. The partial peptide includes a peptide having an amino acid sequence represented by amino acid numbers of 5 to 154 in SEQ ID NO: 2. DNA coding for the partial peptide includes DNA having a base sequence represented by nucleotide numbers of 322 to 771 in SEQ ID NO: 1.

An antibody for binding C6ST can be prepared by using C6ST, the partial peptide thereof, or a fusion protein of any one of them with another protein produced as described above. The antibody may be prepared in the same manner as in preparation of an ordinary antibody. In addition, a monoclonal antibody for binding C6ST can be also prepared in accordance with an ordinary method.

According to the present invention, the DNA coding for the chondroitin 6-sulfotransferase (C6ST) which transfers sulfate group to the hydroxyl group at C-6 position of N-acetylgalactosamine residue or galactose residue of glycosaminoglycan, the polypeptide expressed from the DNA fragment originating from the DNA, and the antibody reactive with the polypeptide are obtained.

The DNA coding for C6ST has been obtained according to the present invention. Thus it is expected to mass-produce C6ST to such a degree that this enzyme can be industrially used.

DESCRIPTION OF PREFERRED EMBODIMENT

Figure 1:
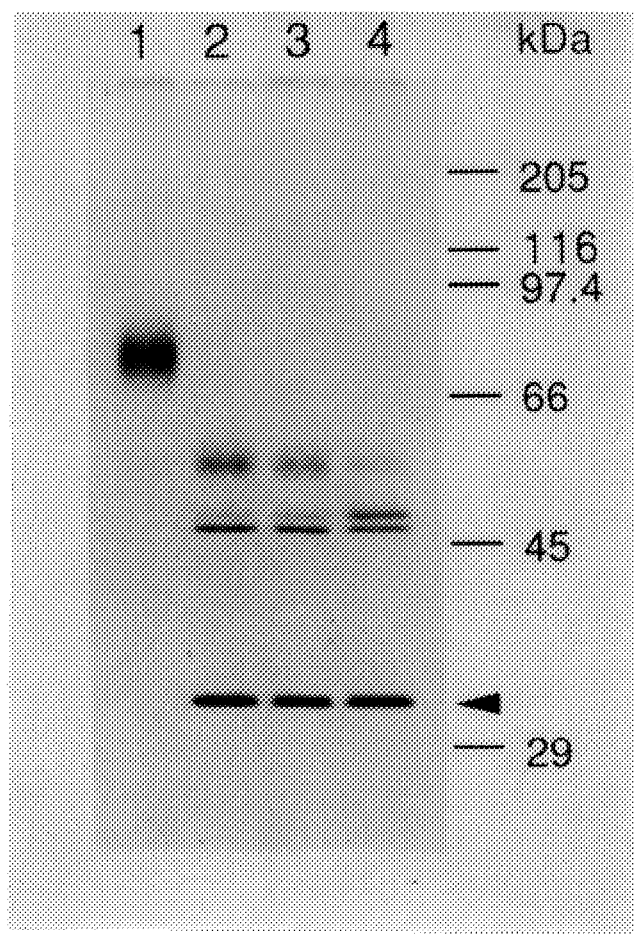
FIG. 1 is a photograph of electrophoresis of purified C6ST and N-glycanase-digested C6ST. Lane 1: intact C6ST; Lanes 2, 3, and 4: C6ST digested with N-glycanase for 1 hour, 2 hours, and 12 hours respectively.

The present invention will be more specifically explained below with reference to examples.

<1>Preparation Of Chondroitin 6-Sulfotransferase And Amino Acid Sequence Analysis (1) Preparation of chondroitin 6-sulfotransferase Chick embryo chondrocytes were inoculated to culture dishes to give a density of $5.6 \times 10^4$ cells/dish, and they were cultured at 38° C. for 11 days under a condition of 7% $CO_2$ and 93% air in Dulbecco's Modified Eagle's medium (DMEM) adjusted at pH 7.0 containing D-glucose (2 g/L), penicillin (100 units/ml), streptomycin (50 μg/ml), and fetal bovine serum (FBS, 10%). The medium was exchanged for a fresh medium at pH 7.4 on 2nd, 4th, 7th, 9th, and 10th days after the start of cultivation.

A medium, containing heat-inactivated serum (10%) prepared by heating FBS at 60° C. for 60 minutes, was used on 10th day. The cells grew up to $5.0 \times 10^6$ cells/dish on 11th day. After that, cultivation was continued for 10 days while exchanging the medium every day by using Cosmedium-001 (purchased from Cosmo Bio) supplemented with sodium ascorbate (50 μg/ml).

The used Cosmedium-001 medium was collected and centrifuged at 10,000×g for 10 minutes to make adjustment so that a supernatant had a composition of 10 mM Tris-HCl, pH 7.2, 0.1% Triton X-100, 20 mM MgCl2, 10 mM 2-mercaptoethanol, and 20% glycerol.

The culture supernatant was applied to a Heparin-Sepharose CL6B column (produced by Pharmacia LKB Biotechnology, 2.2×28 cm) equilibrated with buffer A (10 mM Tris-HCl, pH 7.2, 0.1% Triton X-100, 20 mM $MgCl_2$, 2 mM $CaCl_2$, 10 mM 2-mercaptoethanol, and 20% glycerol) containing 0.15M NaCl. The column was washed with buffer A containing 0.15M NaCl, followed by elution with a linear gradient (1 L) of buffer A containing 0.15 to 0.75M NaCl to perform fractionation by 12 ml/fraction.

Fractions having the sulfotransferase activity were collected and applied to a wheat germ agglutinin-agarose column (produced by Seikagaku Corp., 1.2×15 cm) equilibrated with buffer A containing 0.15M NaCl. The column was washed with buffer A (200 ml) containing 0.15M NaCl, followed by elution with buffer A (200 ml) containing 0.15M NaCl and 0.3M N-acetylglucosamine. Eluted fractions were collected and dialyzed against buffer A containing 0.05M NaCl.

The dialyzed solution of the eluted fractions was applied to a 3', 5'-ADP-agarose column (produced by Sigma, 1.2× 11.8 cm, 1.9 μmol 3',5'-ADP/ml gel) equilibrated with buffer A containing 0.05M NaCl. The column was washed with buffer A (150 ml) containing 0.05M NaCl, followed by elution with a linear gradient (300 ml) of buffer A containing 0.05M NaCl and containing 0 to 0.2 mM 3', 5'-ADP. Fractions having the sulfotransferase activity were collected and dialyzed against buffer A containing 1M NaCl and thereafter against buffer A containing 0.05M NaCl.

The sulfotransferase activity was measured as follows in the purification steps described above. The reaction solution had the following composition: 2.5 μmol of imidazole-HCl (pH 6.8), 1.25 μg of protamine hydrochloride, 0.1 μmol of dithiothreitol, 25 nmol (as an amount of glucuronic acid) of chondroitin (produced by Seikagaku Corp.), 50 pmol of [$^{35}$S]PAPS (adenosine 3'-phosphate, 5'-phosphosulfate), and an enzyme (total 50 μl).

The activity on various glycosaminoglycans as the substrate was measured by using 25 nmol of glycosaminoglycan (as an amount of galactosamine for chondroitin sulfate and dermatan sulfate, or as an amount of glucosamine for heparan sulfate and keratan sulfate) instead of chondroitin.

The reaction solution was incubated at 37° C. for 20 minutes. After that, the reaction was stopped by immersing a reaction tube in boiling water for 1 minute. After the stop of the reaction, 0.1 μmol (as an amount of glucuronic acid) of chondroitin sulfate A was added as a carrier, and 3 volumes of ethanol containing 1.3% potassium acetate was added to precipitate $^{35}$S-labeled polysaccharide. The mixture solution was centrifuged at 10,000×g for 10 minutes, and an obtained precipitate was dissolved in 70 μl of water. This solution (50 μl) was injected into a desalting column equilibrated with 0.1M $NH_4HCO_3$. Eluted fractions containing $^{35}$S-labeled polysaccharide were collected. A scintillation cocktail (Clearsol, produced by Nakarai Tesque, 1 ml) was added to each of aliquots (200 μl) of the obtained fractions, to measure $^{35}$S-radioactivity. Thus incorporation of $^{35}$S into polysaccharide was measured.

An aliquot (400 μl) was taken from the remaining solution, to which ethanol (800 μl) containing 1.3% potassium acetate was added and mixed. The mixture solution was placed on ice for 30 minutes, followed by centrifugation at 10,000×g for 10 minutes to precipitate $^{35}$S-polysaccharide. The precipitate was dissolved in buffer (25 μl) containing 0.1 mg/ml of BSA, 0.05M Tris-acetate (pH 7.5), and 10 milliunits of chondroitinase ACII (from Arthrobacter aurescens, produced by Seikagaku Corp.), and reacted at 37° C. for 2 hours. Reaction products were spotted onto Whatman No. 1 filter paper together with each 0.1 μmol of 2-acetamide-2-deoxy-3-O-(β-D-gluco-4-enepyranosyluronic acid)-6-O -sulfo-D-galactose (ΔDi-6S) and 2-acetamide-2-deoxy-3-O-(β-D-gluco-4-enepyranosyluronic acid) -4-O-sulfo-D-galactose (ΔDi-4S) (both produced by Seikagaku Corp.), and developed for 20 hours with 1-butanol/acetic acid/1M ammonium hydroxide (2:3:1 (v/v/v)).

Positions of ΔDi-6S and ΔDi-4S were inspected with an ultraviolet lamp. Respective sites were excised from the filter paper, and they were immersed in a scintillator prepared by dissolving diphenyloxazole (5 g) and dimethyl 1,4-bis (2-(5-phenyloxazole)) benzene (0.25 g) in 1 L of toluene to measure the radioactivity. In the case of a sample digested with chondroitinase ACII, the radioactivity remaining at the origin on the filter paper was not more than 1% of the spotted radioactivity. The chondroitin 6-sulfotransferase activity and the chondroitin 4-sulfotransferase activity were calculated from incorporation of $^{35}$S into ΔDi-6S and ΔDi-4S respectively. An amount of the activity to catalyze transfer of 1 pmol sulfate group/minute was defined as 1 unit. As a result, the chondroitin 6-sulfotransferase had a specific activity of $4.3 \times 10_5$ units/mg, and the ratio of chondroitin 4-sulfotransferase activity/chondroitin 6-sulfotransferase activity was 0.02.

C6ST purified as described above formed a single band on SDS-PAGE under a reduced condition, and its molecular weight was determined to be 75,000. As a result of measurement by using Superose 12 HR 10/30 gel filtration chromatography (eluent: 10 mM Tris-HCl, pH 7.2, 2M NaCl, 20 mM MgCl2, 2 mM CaCl$_2$, 0.1% Triton X-100, and 20% glycerol), the molecular weight was 160,000. According to this fact, it was suggested that C6ST formed a dimer in the presence of 2M NaCl.

The sulfotransferase activity was measured for various substrates. As a result, it has been demonstrated that C6ST obtained as described above transfers sulfate group to chondroitin, chondroitin sulfate originating from chick embryo cartilage, chondroitin sulfate A, chondroitin sulfate C, and keratan sulfate originating from cornea, but it scarcely transfers sulfate group to chondroitin sulfate E, dermatan sulfate, and heparan sulfate. It has been confirmed by the present inventors that C6ST of the present invention transfers sulfate group to the hydroxyl group at the C-6 position of galactose residue in the case of keratan sulfate.

The activity of C6ST of the present invention was increased by protamine and MnCl$_2$.

The optimum reaction pH of C6ST in the aforementioned measurement system was about 6.4.

(2) Analysis Of Amino Acid Sequence Of Chondroitin 6-Sulfotransferase (C6ST)

Purified C6ST was digested with N-glycanase. Namely, trichloroacetic acid (200 μl) was added to a C6ST solution (1 ml, 10 μg as protein), and was placed on ice for 30 minutes, followed by centrifugation at 10,000×g for 20 minutes. A precipitate was washed twice with 1 ml of acetone, and it was dried in a vacuum desiccator. The dried C6ST protein was dissolved in 0.15M Tris-HCl (pH 7.8, 10 μl) containing 0.5% SDS, and it was heated at 100° C. for 3 minutes, and after cooling, 5 μl of 7.5% (w/v) Nonidet P-40, 1.2 μl of 0.25M EDTA (pH 8), 0.3 μl of phenyl-methanesulfonyl fluoride, 10.5 μl of water, and 3 μl (0.75 unit) of recombinant N-glycanase (produced by Genzyme) were added. The mixed solution was incubated at 37° C. for 12 hours to perform a deglycosylation reaction.

C6ST deglycosylated as described above (10 μg) and intact (non-deglycosylated) C6ST (20 μg) were applied to 10% SDS-PAGE. FIG. 1 shows an image of silver staining after SDS-PAGE for C6ST with a protein amount of 0.6 μg. As for Lanes 2, 3, and 4, the N-glycanase treatment was performed for 1 hour, 2 hours, and 12 hours respectively. Complete C6ST formed a broad band in SDS-PAGE (Lane 1 in FIG. 1). This phenomenon was considered to be caused by microheterogeneity of N-bonded oligosaccharide attached to this enzyme. On the other hand, when C6ST was digested with N-glycanase, then a protein band of 75 kDa disappeared, and two sharp bands (49 kDa and 47 kDa) appeared (Lanes 2 to 4 in FIG. 1).

For the purpose of amino acid sequence analysis, transfer to a polyvinylidene fluoride (PVDF) membrane was performed without staining the gel after SDS-PAGE. This membrane was stained with Coomassie Brilliant Blue. Bands of proteins (49 and 47 kDa) after the N-glycanase digestion and a band of the non-digested protein (75 kDa) were excised from the membrane, and were used for amino acid sequence determination.

On the other hand, in order to determine an internal amino acid sequence of C6ST, a C6ST peptide partially digested with protease was prepared. This experiment was performed in accordance with a method of Cleveland et al. (Cleveland, D. W., Fischer, S. G., Kirshner, M. W., and Laemmli, U. K. (1977) *J. Biol. Chem.* 252, 1102–1106). Namely, the purified protein (30 μg) was separated by SDS-PAGE by using a 10% gel. After the gel was stained with Coomassie Brilliant Blue, the protein band of 75 kDa was excised, and it was inserted into a well in another 16% gel. The well was superimposed by buffer containing protease V8 (sequencing grade, produced by Boehringer Mannheim) in a ratio of 0.05 μg/μg purified protein to start SDS-PAGE. The power source was turned off when a forward end of a dye arrived at an end of a separating gel. The electrophoresis was started again after 30 minutes. Peptides formed by the protease digestion were transblotted to a PVDF membrane. This membrane was stained with Coomassie Brilliant Blue, and then a peptide ban d of 19 kDa was excised.

The PVDF filters containing the proteins produced after the N-glycanase digestion, the intact protein, and the peptide pr oduced after the protease V8 digestion prepared as described above respectively were sent to Takara Shuzo Co., Ltd. (Kyoto). We entrusted Takara Shuzo with the determination of amino acid sequences of amino terminals. Results are shown in Table 1.

TABLE 1

| | | |
|---|---|---|
| 49-kDa protein | LVIXXXXNNFIXXV | (SEQ ID NO: 3) |
| 47-kDa protein | XVIXEXXNNFIXXV | (SEQ ID NO: 4) |
| Intact protein | LVIXEKENNFISRVSDKLKXXPXV | (SEQ ID NO: 5) |
| 19-kDa peptide | SFISPAPEEXLTA | (SEQ ID NO: 6) |

Figures 2, 3:
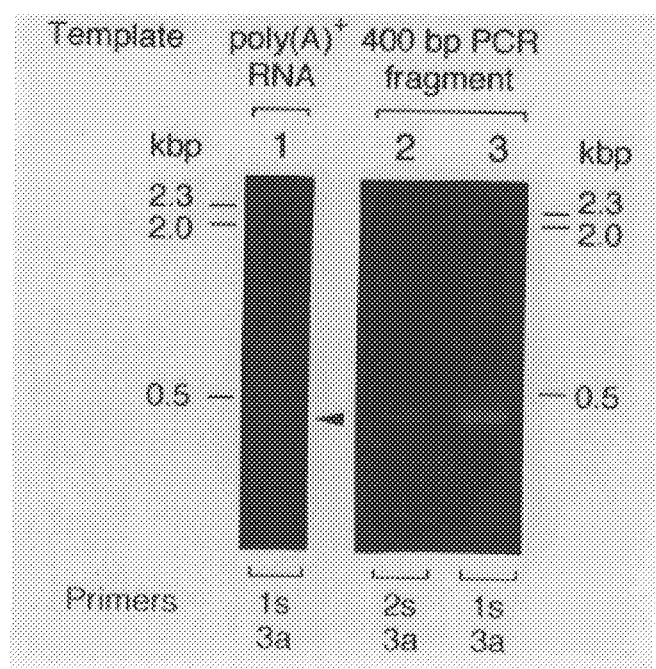
FIG. 2 is partial amino acid sequences of C6ST and sequences of primers for PCR.
FIG. 3 shows a photograph of electrophoresis of partial cDNA of C6ST amplified by PCR. Lanes 1 and 3: Oligonucleotides 1s and 3a were used as primers; Lane 2: Oligonucleotides 2s and 3a were used as primers. Poly(A)$^+$RNA was used as a template in Lane 1. A PCR product amplified from poly(A)$^+$RNA by using oligonucleotides 1s and 3a as primers was used as a template in Lanes 2 and 3.

<2>Amplification of Partial CDNA of C6ST By PCR (1) Preparation Of Primers For PCR Oligonucleotide primers were prepared to amplify C6ST cDNA clone from a cDNA library by means of PCR on the basis of the amino acid sequences determined as described above. The oligonucleotide primers were designed as shown in FIG. 2. Two sense primers (primer 1s (SEQ ID NO: 7) and primer 2s (SEQ ID NO: 8)) were synthesized on the basis of the amino acid sequence (SEQ ID NO: 5) obtained from the intact C6ST protein (75 kDa). An antisense primer (primer 3a (SEQ ID NO: 9)) was synthesized on the basis of the amino acid sequence (SEQ ID NO: 6) obtained from the peptide (19 kDa) obtained by the protease digestion.

A base sequence containing a HindIII recognition sequence was introduced into a 5'-terminal of the primer 1s. A base sequence containing an EcoRI recognition sequence was introduced into a 5'-terminal of the primer 3a.

(2) Preparation of poly(A)$^+$RNA

Total RNA was prepared in accordance with the guanidine thiocyanate/CsCl method (Kingston, R. E., (1991) in *Current Protocols in Molecular Biology*, Suppl. 14, Unit 4.2, Greene Publishing Associates and Wiley Interscience, New York) from chick embryo chondrocytes cultured for 11 days in Dulbecco's Modified Eagle's medium (DMEM) containing 10% fetal bovine serum in accordance with a known method (Kim, J. J. and Conrad, H. E. (1976) *J. Biol. Chem.* 251, 6210–6217; Kim, J. J. and Conrad, H. E. (1977) *J. Biol. Chem.* 252, 8292–8299; Kim, J. J. and Conrad, H. E. (1980) *J. Biol. Chem.* 255, 1586–1597). Poly(A)$^+$RNA was purified from the obtained total RNA by means of oligo(dT) cellulose column chromatography.

(3) PCR reaction

A cDNA primary strand was synthesized by using the poly(A)$^+$RNA described above as a template in accordance with a reverse transcription reaction by using the oligonucleotide 3a as a primer. The reverse transcription reaction was performed by incubating a buffer (final volume 20 μl) containing poly(A)$^+$RNA (1 μg), oligonucleotide 3a (50 pmol), four species of deoxynucleoside triphosphates (each 500 μM), M-MLV reverse transcriptase (200 units, produced by Gibco BRL), dithiothreitol (1 mM), and RNase inhibitor (120 units, produced by Takara Shuzo) at 37° C. for 60 minites.

A PCR reaction was performed in a reaction solution (final volume 100 μl) containing the reverse transcription reaction mixture described above (10 μl), oligonucleotides 1s and 3a (each 50 pmol), four species of deoxynucleoside triphosphate (each 100 μM), and Taq polymerase (2.5 units, AmpliTaq polymerase, produced by Perkin-Elmer). The amplification reaction was performed in 30 cycles of a repeating reaction cycle composed of periods at 94° C. for 1 minute, 45° C. for 1 minute, and 55° C. for 3 minutes.

Reaction products were subjected to agarose gel electrophoresis. As a result, DNA fragments of 400 and 600 bp were observed (FIG. 3, Lane 1). Among the amplified products, the product of 400 bp was considered to be specific because of the following reason. Namely, when a PCR reaction was performed by using the primers 2s and 3a as primers and using the fragment of 400 bp as a template, then a fragment slightly shorter than the template was amplified (FIG. 3, Lane 2). Further, a base sequence of the fragment of 400 bp was determined. As a result, it was found that the fragment of 400 bp compirsed 465 nucleotides in which a base sequence corresponding to the primer 2s exists in the vicinity of a sequence corresponding to the primer 1s, demonstrating that the fragment was amplified from mRNA of the C6ST protein.

<3>Preparation Of Entire Length cDNA of C6ST (1) Preparation of probe for hybridization The amplified fragment of 400 bp described above (shown by an arrow in FIG. 3) was recovered from the gel, digested with HindIII and EcoRI, and subcloned into cleavage sites of these restriction enzymes of Bluescript (produced by Stratagene) as a plasmid vector. A subclone was confirmed by sequencing by using T3 primer or M13–20 primer.

A radioactive probe for screening a cDNA library was obtained by radiolabeling the PCR product described above in accordance with a random oligonucleotide-primed labeling method (Feinberg, A. P. and Vogelstein, B. (1983) *Anal. Biochem.* 132, 6–13) by using [α-$^{32}$p]dCTP (produced by Amersham) and a DNA random labeling kit (produced by Takara Shuzo).

(2) Construction of cDNA library

Next, in order to obtain cDNA containing an entire length of the coding region of C6ST, a lambda vector, λgt11 was used to perform cDNA cloning.

Poly(A)$^+$RNA was prepared from chick embryo chondrocytes in the same manner as described in the foregoing item <2>(2), and was used as a template to synthesize double strand cDNA. The DNA was ligated with λgt11 having been digested with EcoRI (EcoRI-digested λgt11, produced by Pharmacia). A cDNA synthesis kit (TimeSaver cDNA synthesis kit, produced by Pharmacia) was used for the synthesis of cDNA and the ligation with the vector. Random oligonucleotide primers were used as a primer for the reverse transcription reaction.

The recombinant phage vector with inserted cDNA was packaged into phage particles by using an in vitro packaging kit (Gigapack II packaging extract, produced by Stratagene). *Escherichia coli* Y1088 was infected with the phage particles, and was layered on a plate to form plaques. A phage library thus obtained was used for cDNA screening without further amplification.

(3) Screening for C6ST cDNA clone

Screening was performed for about 5×10$^5$ plaques of the λgt11 cDNA library obtained as described above. Plaques were transferred onto a commercially available nylon membrane (Hybond N$^+$nylon membrane, produce by Amersham), and phage DNA was immobilized onto the nylon membrane in accordance with an alkaline immobilizing method recommended in a manual appended to the commercial product.

The membrane having immobilized phage DNA thereon was subjected to prehybridization at 42° C. for 3.5 hours in a solution containing 50% formamide, 5×SSPE (composition of 1×SSPE: 10 mM NaH$_2$PO$_4$ (pH 7.4), 150 mM NaCl, 1 mM EDTA), 5×Denhardt's solution (composition of 1×Denhardtxs solution: 0.02% Ficoll 400, 0.02% polyvinylpyrrolidone, 0.02% BSA), 0.5% SDS, 0.04 mg/ml of denatured salmon sperm DNA, and 0.004 mg/ml of *E. coli* DNA. Hybridization was performed at 42° C. for 16 hours in the same buffer as described above containing the 32p-labeled probe. After that, the filter was washed at 55° C. in 1×SSPE (0.1% SDS) and thereafter in 0.1×SSPE (0.1% SDS), and then hybridization-positive clones were detected by means of autoradiography. About 90 positive clones were obtained from 5×105 plaques.

(4) Base sequence analysis for C6ST cDNA

Independent clones (16 individuals) were selected from the hybridization-positive λgt11 clones. Phage DNA's were prepared respectively, and they were digested with EcoRI for excising single fragments of cDNA insertion fragments from the vector DNA's. These cDNA fragments were subcloned into Bluescript. A fragment (2.3 kb), which was longest among these cDNA fragments, was used to determine its base sequence.

A deletion clone was prepared from the recombinant plasmid obtained by subcloning cDNA into Bluescript, by using a DNA deletion kit (produced by Takara Shuzo) in accordance with a known method (Henikoff, S. (1984) *Gene* 28, 351–359; Yanisch-Perron, C., Viera, J., and Messing, J. (1985) *Gene* 33, 103–109). SacI and XbaI were used as a restriction enzyme for leaving a 3'-cohesive end and a restriction enzyme for leaving a 5'-cohesive end, respectively.

An obtained deletion clone was used to independently determine base sequences of both strands in accordance with the dideoxy chain termination method (Sanger, F., Nicklens, S., and Coulson, A. R. (1977) *Proc. Natl. Acad. Sci. U.S.A.* 74, 5463–5467) by using [α-$^{32}$p]dCTP and T7 DNA polymerase (Sequenase, produced by U.S. Biochemical). A base sequence of C6ST cDNA thus determined and a deduced amino acid sequence are shown in SEQ ID NO: 1. Only the amino acid sequence i s shown in SEQ ID NO: 2.

The determined DNA sequence was analyzed by using Gene Works computer programs (produced by IntelliGenetics). Two in-frame ATG codons are contained in a 5'-terminal portion of an open reading frame of C6ST cDNA. A single open reading frame starting from the first ATG codon suggests a protein containing 458 amino acid residues with a molecular weight of 52,193 and having six sites which possibly serve as N-binding glycosylation sites.

Figure 4:
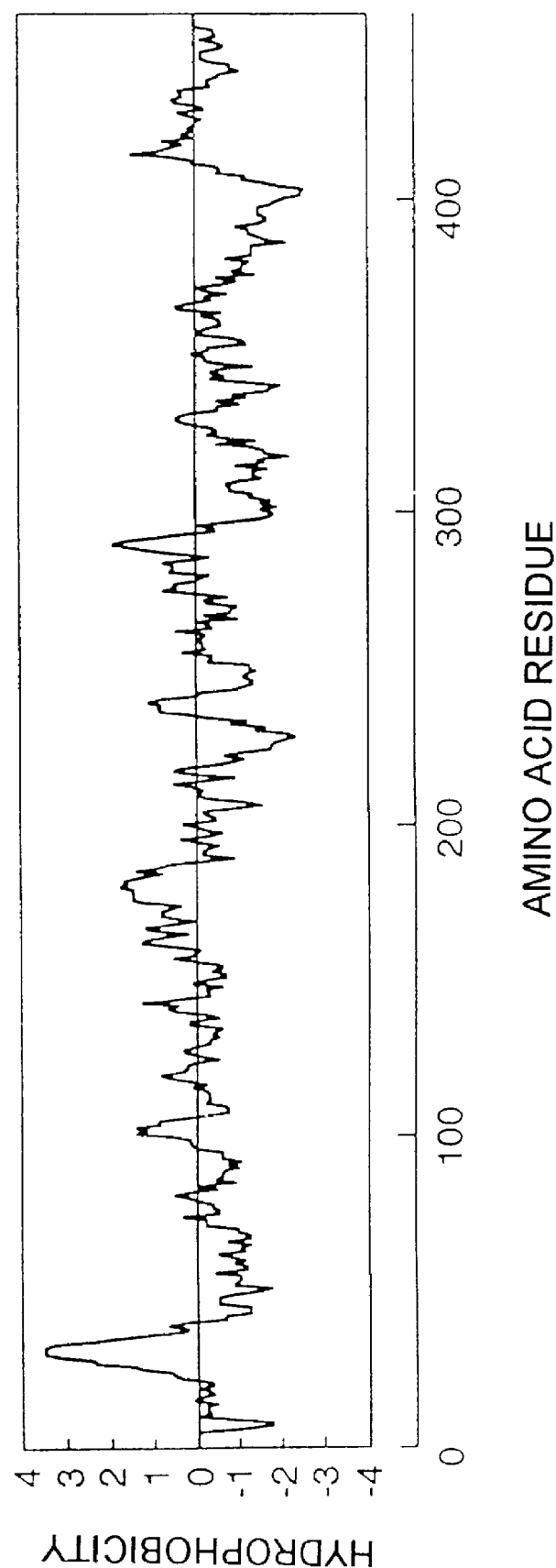
FIG. 4 shows a hydropathy plot of an amino acid sequence deduced from a cDNA sequence.

A hydropathy plot was prepared from the deduced amino acid sequence (FIG. 4) in order to clarify whether or not the protein would have a transmembrane domain, and determine, if any, its position. The hydropathy plot was calculated by using a window of 11 amino acids in accordance with a method of Kyte et al. (Kyte, J. and Doolittle, R. F., (1982) *J. Mol. Biol.* 157, 105–132). As a result of analysis of the plot, a conspicuous hydrophobic portion having a le ngth of 14 residues ranging from 24th to 37th amino acid residues as counted from the N-terminal was found at an amino terminal portion (FIG. 4), which was estimated as a transmembrane domain (amino acid numbers of −10 to 4 in SEQ ID NO: 2). The amino acid sequence of the amino terminal of the purified intact C6ST was found in the transmembrane domain. If the protein is cut at the boundary of the transmembrane domain, its molecular weight is calculated to be 47,885 which is well coincident with the molecular weight of the protein formed after the N-glycanase digestion. All of the amino acid sequences obtained from the purified protein were found in the deduced sequence of the protein. Thus it has been confirmed that the cDNA clone codes for C6ST. Further, it is considered that C6ST is expressed as a precursor, and the N-terminal portion is removed during permeation through the membrane to generate a mature protein comprising 425 amino acid residues. <4>Expression Of C6ST cDNA (1) Construction of C6ST expression plasmid In order to express C6ST cDNA, the cDNA fragment was introduced into an expression vector to construct a recombinant plasmid. An expression vector for mammalian cells pCXN2 (constructed by Dr. Jun-ichi Miyazaki of the University of Tokyo (Niwa, H., Yamamura, K., and Miyazaki, J. (1991) *Gene* 108, 193–200) and kindly given by Dr. Yasuhiro Hashimoto of Tokyo Metropolitan Institute of Medical Science) was used as the expression vector. pCXN2 is a vector which has a streptomycin resistance gene and a penicillin resistance gene, and can express a DNA fragment inserted into an EcoRI site by using a β-actin gene promoter. The cDNA fragment of 2,354 bp (SEQ ID NO: 1) was ligated to the EcoRI site of pCXN2. *E. coli* JM109 was transformed with a reaction solution after the ligation, and it was applied onto an LB plate containing ampicillin. Recombinant plasmids were recovered from transformants, and they were purified by three times of CsCl/ethidium bromide equilibrium centrifugation. A recombinant plasmid, in which the promoter of the vector and cDNA had a coincident direction, was designated as pCXNC6ST. A recombinant plasmid, in which cDNA was inserted in an opposite direction, was designated as pCXNC6ST2. The direction of cDNA was analyzed by restriction mapping by using BamHI.

(2) Transient expression of C6ST cDNA in COS-7 cells

COS-7 cells were used as a host for expressing C6ST cDNA. COS-7 cells (obtained from RIKEN GENE BANK, Tsukuba) were sown on culture dishes having a diameter of 100 mm at a density of $8 \times 10^5$ cells/dish. Dulbeccol's Modified Eagle's medium (DMEM) containing penicillin (100 units/ml), streptomycin (50 μg/ml), and 10% fetal bovine serum (produced by Gibco BRL) was used as a culture liquid in an amount of 10 ml per culture dish. Cells were cultured in 5% $CO_2$ and 95% air at 37° C.

COS-7 cells were transfected with pCXNC6ST or pCXNC6ST2 when the cell density arrived at $3 \times 10^6$ cells/dish (after 48 hours of cultivation). The transfection was performed in accordance with the DEAE-dextran method (Aruffo, A. (1991) in *Current Protocols in Molecular Biology*, Suppl. 14, Unit 16.13, Greene Publishing Associates and Wiley Interscience, New York). Previously warmed DMEM (5 ml) containing 10% Nu serum (a serum substitute having a low protein concentration, produced by Collaborative Biomedical Products) was mixed with PBS (phosphate-buffered saline, 0.2 ml) containing DEAE-dextran (10 mg/ml) and chloroquine solution (2.5 mM). This solution was mixed with 15 μg of the recombinant plasmid, and a resulting mixture was added to the cell suspension.

The cells were incubated for 4 hours in a $CO_2$ incubator. After that, the culture liquid was substituted with a PBS solution (5 ml) containing 10% dimethyl sulfoxide (DMSO). The cells were left at room temperature for 2 minutes. After that, the dimethyl sulfoxide solution was removed by aspiration, followed by addition of 25 ml of DMEM containing penicillin (100 units/ml), streptomycin (50 μg/ml), and 10% fetal bovine serum. The cells were incubated for 67 hours, and then they were washed with only DMEM. The cells were collected and homogenized by using Dounce homogenizer in a solution containing 0.25M sucrose, 10 mM Tris-HCl, pH 7.2, and 0.5% Triton X-100, the solution being used in an amount of 1.5 ml per cells obtained from one culture dish. An obtained homogenate was centrifuged at 10,000 ×g for 20 minutes to measure the C6ST activity, the chondroitin 4-sulfotransferase (C4ST) activity, and the keratan sulfate sulfotransferase (KSST) activity in a supernatant fraction. These activities were measured in the presence or absence of chondroitin or keratan sulfate as a sulfate group acceptor. The measurement was performed in the same manner as described above for COS-7 cells which had not been transfected with the expression plasmid. Results are shown in Table 2.

TABLE 2

| Plasmid | C6ST activity | | C4ST activity | | KSST activity | |
| --- | --- | --- | --- | --- | --- | --- |
| | accen-tor(−) | accep-tor(+) | accep-tor(−) | accep-tor(+) | accep-tor(−) | accep-tor(+) |
| | (pmol/minute/mg protein) | | | | | |
| None | 0.3 ± 0.1 | 1.4 ± 0.2 | <0.1 | 0.2 ± 0.1 | <0.1 | 0.5 ± 0.2 |
| pCXNC6ST2 | 0.4 ± 0.1 | 1.7 ± 0.3 | <0.1 | 0.3 ± 0.1 | <0.1 | 0.3 ± 0.1 |
| pCXNC6ST | 4.3 ± 0.8 | 40.4 ± 3.0 | <0.1 | 0.3 ± 0.1 | <0.1 | 4.6 ± 0.2 |

As shown in the table, the C6ST activity and the KSST activity of the cells harboring the expression vector to express the aforementioned isolated cDNA in the correct direction were about 20-fold and about 15-fold respectively as compared with those of the cells harboring the expression vector with cDNA inserted in the opposite direction. However, the C4ST activity of the transfected cells was not increased. According to these results, it has been demonstrated that the isolated cDNA codes for a protein having the C6ST activity.

<5>Preparation Of Antibody Reactive With C6ST (1) Preparation of C6ST fusion peptide A DNA fragment (nucleotide numbers of 322 to 771 in SEQ ID NO: 1), coding for 150 amino acid residues from Glu of an amino acid number of 5 to Ile of an amino acid number of 154 in the amino acid sequence shown in SEQ ID NO: 2, was obtained in the same manner as the DNA fragment of 465 bp amplified by PCR from poly(A)$^+$RNA described in the aforementioned item <2>(3). A sequence containing a BamHI site was introduced into a sense primer starting from Glu$^5$. A sequence containing an EcoRI site was introduced into an antisense primer starting from Ile$^{154}$.

PCR was performed in 30 cycles of a repeating cycle composed of periods at 94° C. for 1 minute, 45° C. for 2 minute, and 72° C. for 2 minutes. A PCR product was digested with EcoRI and BamHI, and it was subcloned into these restriction enzyme sites of pRSET A plasmid (produced by Invitrogen). pRSET A is a plasmid for expressing, under control of T7 promoter, a fusion peptide of a peptide encoded by the inserted fragment and a leader peptide containing six histidines (His).

E. coli DE3 was transfected with an obtained recombinant plasmid to produce the fusion peptide. The fusion peptide was purified by using a resin affinity column charged with $Ni^{2+}$(ProBond Resin, produced by Invitrogen) in accordance with a method described in a manual appended to the commercial product. Proteins contaminating the purified fusion peptide were ultimately removed by means of 15% SDS-PAGE. The fusion peptide of 22 kDa was eluted from a polyacrylamide gel after electrophoresis by using 50 mM Tris-HCl, pH 8.0 containing 150 mM NaCl, 100 mM EDTA, 0.1% SDS, and 5 mM dithiothreitol, and it was precipitated with five volumes of acetone.

(2) Preparation of antibody against fusion peptide

The precipitate of the fusion peptide described above was dissolved in 50 mM Tris-HCl, pH 8.0 containing 6M guanidine hydrochloride, 150 mM NaCl, 0.1 mM EDTA, 0.1% Nonidet P-40, and 1 mM dithiothreitol, and was dialyzed against PBS. The dialyzed fusion peptide solution was intraperitoneally injected into a mouse. A polyclonal antibody (antiserum) was obtained after two times of boost injections.

(3) Assay of antibody and detection of C6ST in chondrocyte culture liquid

The antiserum obtained as described above was assayed by means of immunoblotting. Proteins in a chondrocyte culture liquid cultured in a serum-free medium, the purified C6ST, and the fusion peptide of 22 kDa described above were applied to 12% SDS-PAGE in accordance with the method of Laemmli (Laemmli, U. K. (1970) Nature 227, 680–685), and transferred onto a nitrocellulose filter. Bands of proteins were stained and visualized by using Amide Black. In the case of immunoblotting, the filter was subjected to blocking, and then a diluted solution (1:1000) of the antiserum obtained as described above was added thereto, followed by incubation. The antibody bound to the filter was visualized by an enzyme immunoassay method by using a secondary antibody of peroxidase-conjugated anti-mouse immunoglobulin goat IgG (produced by Cappel).

Figure 5:
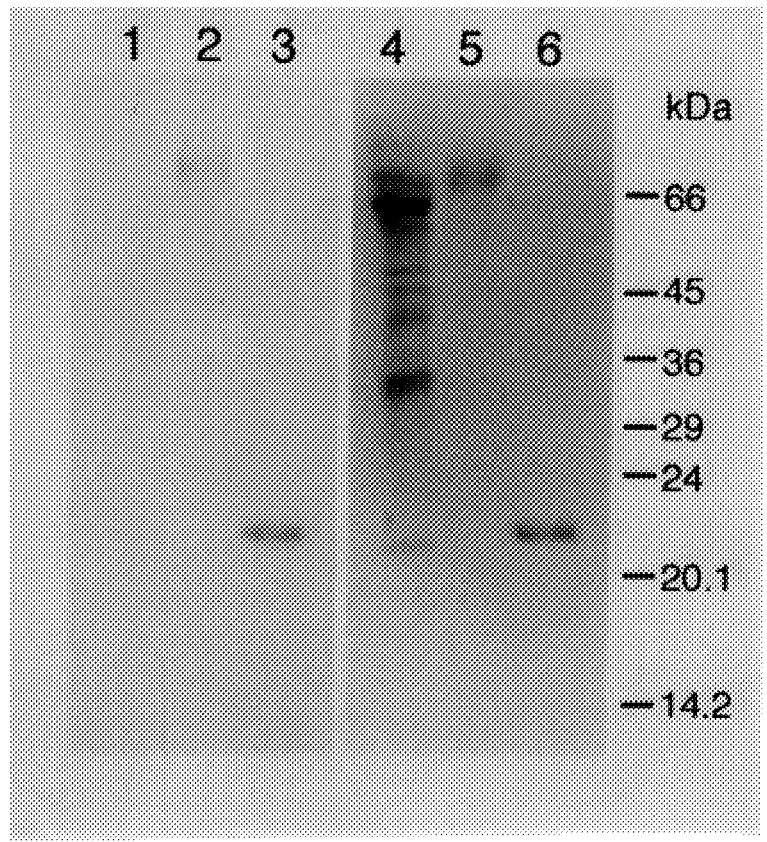
FIG. 5 is a photograph of electrophoresis of proteins in a culture liquid of chondrocytes cultured in a serum-free medium (Lanes 1, 4), purified C6ST (Lanes 2, 5), and 22 kDa fusion peptide (Lanes 3, 6). Lanes 1 to 3 were visualized by immunoblotting, while Lanes 4 to 6 were visualized by Amide Black staining. Amounts of proteins were 12 μg (Lanes 1, 4), 0.4 μg (Lane 2), 0.1 μg (Lane 3), 0.8 μg (Lane 5), and 0.5 μg (Lane 6).

FIG. 5 shows results of Amide Black staining (Lanes 4 to 6) and results of immunoblotting (Lanes 1 to 3). The polyclonal antibody prepared against the fusion peptide of 22 kDa described above cross-reacted with the fusion peptide and the purified C6ST of 75 kDa (FIG. 5, Lanes 2, 3).

The antibody did not react with proteins contained in the culture liquid of chondrocytes (Lane 1). This result was obtained possibly because C6ST was contained in the culture liquid in a minute amount.

(4) Immunoprecipitation of C6ST

The mouse antiserum (3 μl) prepared against the fusion protein of 22 kDa was added to 31 μl of buffer B (10 mM Tris-HCl, pH 7.2, 130 mM NaCl, 10 mM $MgCl_2$, 2 mM $CaCl_2$, 0.1% Triton X-100, 20% glycerol) containing 23 ng of purified C6ST. This mixture was incubated at 4° C. overnight, and then 6 μl of anti-mouse IgG rabbit IgG (produced by Cappel) was added thereto. Incubation was further performed at 0° C. for 1 hour. After that, the reaction mixture was mixed with 20 μl of a suspension of 50% (v/v) protein A-Sepharose (produced by Pharmacia) equilibrated with buffer B, followed by shaking at 4° C. for 30 minutes. An immunocomplex attached to the protein A-Sepharose was removed by centrifugation, and the activity of C6ST remaining in a supernatant solution was measured. The same operation as described above was performed as control by using serum not immunized by the fusion protein, or by adding no serum. Results are shown in Table 3.

TABLE 3

| Added serum | C6ST activity (pmol/minute/ml) |
|---|---|
| None | 125 ± 5 |
| Control serum | 132 ± 3 |
| Anti-fusion peptide serum | 52 ± 10 |

As demonstrated in the table, a major part of the C6ST activity disappeared from the soluble fraction when the anti-fusion peptide serum was added to the purified C6ST solution, and the antibody-C6ST immunocomplex was removed. According to the results, it is also clear that the fusion peptide of 22 kDa contains the amino acid sequence which cannot be immunologically distinguished from C6ST. Thus it has been confirmed that the isolated cDNA codes for the C6ST protein.

Figure 6:
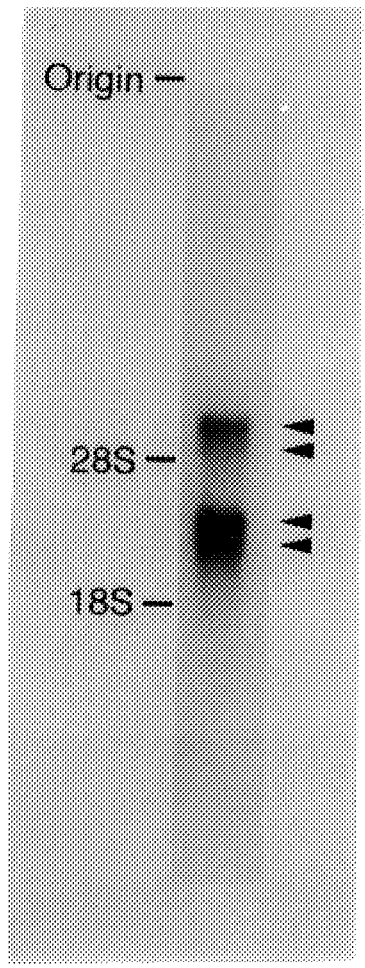
FIG. 6 is a photograph of electrophoresis showing a result of northern blot analysis of poly(A)$^+$RNA from chick chondrocytes.

(5) Analysis of C6ST expression by northern blot analysis of chick chondrocyte poly(A)$^+$RNA Poly(A)$^+$RNA (5 μg) prepared from chick chondrocytes in the same manner as described above was denatured at 65° C. for 10 minutes in a solution containing 50% (v/v) formamide, 5% (v/v) formaldehyde, and 20 mM MOPS (pH 7.0), was subjected to electrophoresis by using 1.2% agarose gel containing 5% (v/v) formaldehyde, and was transferred overnight onto a nylon membrane (Hybond N$^+$, produced by Amersham). The membrane was subjected to thermal fixation at 80° C. for 2 hours to immobilize RNA, and was subjected to prehybridization at 42° C. for 3 hours in a solution containing 50% formamide, 5×SSPE, 5×Denhardt's solution, 0.5% SDS, and 0.1 mg/ml of denatured salmon sperm DNA. This membrane was immersed in the same buffer containing the $^{32}$P-labeled probe, and it was incubated at 42° C. for 14 hours to perform hybridization. The $^{32}$P-labeled probe used in this experiment was the same as that used in the screening for the cDNA library described above. After that, the filter was washed at 65° C. in 2×SSPE (0.1% SDS), and thereafter in 1×SSPE (0.1% SDS). An X-ray film was exposed with this membrane at −80° C. for 26 hours by using a sensitizing screen. As a result, as shown in FIG. 6, four bands having relevant sizes of 5.8, 4.5, 3.2, and 2.5 kb were obtained.

What is claimed is:

1. An isolated polynucleotide encoding a sulfotransferase or enzymatically active fragment thereof which is hybridizable with a polynucleotide complementary to the polynucleotide of SEQ ID NO:1 at 42° C. in a solution containing 50% formamide. 5×SSPE, 5×Denhardt's solution 0.5% SDS, and is stable in subsequent washing at 55° C. with 1×SSPE and with 0.1×SSPE, wherein the sulfotransferase or enzymatically active fragment thereof has activity to transfer sulfate group from a sulfate group donor to the hydroxyl group at C-6 position of N-acetylgalactosamine residue or galactose residue of glycosaminoglycan, wherein said at least a part of a sulfotransferase has the following properties:

(i) action: sulfate group is transferred from a sulfate group donor to the hydroxyl group at C-6 position of N-acetylgalactosamine residue or galactose residue of glycosaminoglycan;

(ii) substrate specificity: sulfate group is transferred to chondroitin, chondroitin sulfate originating from chick embryo cartilage, chondroitin sulfate A, chondroitin sulfate C, and keratan sulfate originating from cornea, but no sulfate group is substantially transferred to chondroitin sulfate E, dermatan sulfate, and heparan sulfate;

(iii) optimum reaction pH: about 6.4;

(iv) inhibition and activation: the activity of this enzyme is increased by protamine and $MnCl_2$; and (v) molecular weight: this enzyme has a molecular weight of about 75,000 estimated by SDS-polyacrylamide gel electrophoresis under a reduced condition, while it has a molecular weight of about 160,000 estimated by gel filtration under a non-reduced condition.

2. An isolated polynucleotide encoding a sulfotransferase or enzymatically active fragment thereof, which is hybridizable with a polynucleotide complementary to the polynucleotide of SEQ ID NO:1 at 42° C. in a solution containing 50% formamide, 5×SSPE, 5×Denhardt's solution, 0.5% SDS, and is stable in subsequent washing at 55° C. with 1×SSPE and with 0.1×SSPE. wherein the sulfotransferase or enzymatically active fragment thereof has activity to transfer sulfate group from a sulfate group donor to the hydroxyl group at C-6 position of N-acetylgalactosamine residue or galactose residue of glycosaminoglycan, said sulfotransferase being derived from a chick chondrocyte.

3. A polynucleotide having a base sequence coding for an amino acid sequence represented by amino acid numbers of −33 to 425 in SEQ ID NO:2.

4. A polynucleotide having a base sequence coding for an amino acid sequence represented by amino acid numbers of −14 to 425 in SEQ ID NO:2.

5. A polynucleotide having a base sequence coding for an amino acid sequence represented by amino acid numbers of 1 to 425 in SEQ ID NO:2.

6. A polynucleotide having a base sequence coding for an amino acid sequence represented by amino acid numbers of 5 to 154 in SEQ ID NO:2.

7. An isolated polynucleotide encoding a part of a sulfotransferase or enzymatically active fragment thereof, which is hybridizable with a polynucleotide complementary to the polynucleotide of SEQ ID NO:1 at 42° C. in a solution containing 50% formamide, 5×SSPE. 5×Denhardt's solution, 0.5% SDS, and is stable in subsequent washing at 55° C. with 1×SSPE and with 0.1×SSPE, wherein the sulfotransferase or enzymatically active fragment thereof has activity to transfer sulfate group from a sulfate group donor to the hydroxyl group at C-6 position of N-acetylgalactosamine residue or galactose residue of glycosaminoglycan, wherein said part of a sulfotransferase exhibits antigenicity of the sulfotransferase having the following properties:

(I) action: sulfate group is transferred from a sulfate group donor to the hydroxyl group at C-6 position of N-acetylgalactosamine residue or galactose residue of glycosaminoglycan;

(ii) substrate specificity: sulfate group is transferred to chondroitin, chondroitin sulfate originating from chick embryo cartilage, chondroitin sulfate A, chondroitin sulfate C, and keratan sulfate originating from cornea, but no sulfate group is substantially transferred to chondroitin sulfate E, dermatan sulfate, and heparan sulfate;

(iii) optimum reaction pH: about 6.4;

(iv) inhibition and activation: the activity of this enzyme is increased by protamine and $MnCl_2$; and (v) molecular weight: this enzyme has a molecular weight of about 75,000 estimated by SDS-polyacrylamide gel electrophoresis under a reduced condition, while it has a molecular weight of about 160,000 estimated by gel filtration under a non-reduced condition.

8. An isolated polynucleotide according to claim 7, wherein said sulfotransferase being derived from a chick chondrocyte.

9. An isolated polynucleotide according to claim 1, wherein said polynucleotide encodes an enzymatically active polypeptide having at least a part of the sequence of SEQ ID NO:2.

10. A vector comprising an isolated polynucleotide of claim 1, said vector capable of transfecting a host cell to express the isolated polynucleotide.

11. A vector comprising an isolated polynucleotide of claim 9; said vector capable of transfecting a host cell to express the isolated polynucleotide.

12. A host cell for producing a sulfotransferase or enzymatically active fragment thereof, which is transfected with a vector of claim 10.

13. A host cell for producing a sulfotransferase or enzymatically active fragment thereof, which is transfected with a vector of claim 11.

14. An expression system for producing a sulfotransferase or enzymatically active fragment thereof, comprising a host cell of claim 12.

15. An expression system for producing a sulfotransferase or enzymatically active fragment thereof, comprising a host cell of claim 13.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 2354
        ( B ) TYPE: nucleic acid
        ( C ) STRANDEDNESS: both
        ( D ) TOPOLOGY: linear ( i i ) MOLECULE TYPE: cDNA to mRNA ( v i ) ORIGINAL SOURCE:
        ( A ) ORGANISM: Chick
        ( B ) TISSUE TYPE: Embryo chondrocyte ( i x ) FEATURE:
        NAME/KEY: CDS
        LOCATION: 211..1584
        IDENTIFICATION METHOD: P ( i x ) FEATURE:
        NAME/KEY: sig_peptide
        LOCATION: 211..309
        IDENTIFICATION METHOD: P ( i x ) FEATURE:
        NAME/KEY: mat_peptide
        LOCATION: 310..1584
        IDENTIFICATION METHOD: P ( i x ) FEATURE:
        NAME/KEY: transmembrane domain
        LOCATION: 280..321
        IDENTIFICATION METHOD: P ( i x ) FEATURE:
        NAME/KEY: potential N-glycosilation site
        LOCATION: 394..402
        IDENTIFICATION METHOD: S ( i x ) FEATURE:
        NAME/KEY: potential N-glycosilation site
        LOCATION: 427..435
        IDENTIFICATION METHOD: S ( i x ) FEATURE:
        NAME/KEY: potential N-glycosilation site
        LOCATION: 493..501
        IDENTIFICATION METHOD: S ( i x ) FEATURE:
        NAME/KEY: potential N-glycosilation site
        LOCATION: 916..924
        IDENTIFICATION METHOD: S ( i x ) FEATURE:
        NAME/KEY: potential N-glycosilation site
        LOCATION: 1405..1413
        IDENTIFICATION METHOD: S ( i x ) FEATURE:
        NAME/KEY: potential N-glycosilation site
        LOCATION: 1537..1545
        IDENTIFICATION METHOD: S ( x i ) SEQUENCE DESCRIPTION: SEQ ID NO:1:

```
CCGTGAAGAA  AAGCAGGGCC  CCCGCCGCCC  GCCCCGCCGC  ACCGCACGAC  CGGGCCCTCG        60

CGGGCCAGAA  CCACCTGGGA  AGGGATGCTG  CGGGACGGCA  GGTGCCCTGC  AGATAGCCCA       120

GGGCATCAGG  TGCCTGCCTG  GGGGATCCTC  TGAGGACAAC  ATGGACATGC  AGAGGACACA       180
```

-continued

| | | | | | | | | | | | | |
|---|---|---|---|---|---|---|---|---|---|---|---|---|
| AAAGGTGTAG | CTCCCTCACT | CACCGTCCCA | ATG<br>Met<br>-33 | GAG<br>Glu | AGG<br>Arg | AGA<br>Arg | TCA<br>Ser | GCT<br>Ala<br>-30 | TTG<br>Leu | CCC<br>Pro | | 234 |
| CAG<br>Gln<br>-25 | GAT<br>Asp | TTT<br>Phe | CGG<br>Arg | GAG<br>Glu | GTG<br>Val<br>-20 | CTG<br>Leu | CAC<br>His | TGC<br>Cys | CTG<br>Leu | AAG<br>Lys<br>-15 | ATG<br>Met | AGG<br>Arg | AGC<br>Ser | AAG<br>Lys | TAT<br>Tyr<br>-10 | 282 |
| GCC<br>Ala | GTG<br>Val | CTG<br>Leu | CTG<br>Leu | GTG<br>Val<br>-5 | TTC<br>Phe | GTG<br>Val | GTG<br>Val | GGG<br>Gly | CTA<br>Leu<br>1 | GTC<br>Val | ATC<br>Ile | ATC<br>Ile | GAG<br>Glu<br>5 | AAG<br>Lys | GAA<br>Glu | 330 |
| AAC<br>Asn | AAC<br>Asn | TTC<br>Phe<br>10 | ATC<br>Ile | TCC<br>Ser | AGG<br>Arg | GTG<br>Val | TCG<br>Ser<br>15 | GAC<br>Asp | AAG<br>Lys | CTG<br>Leu | AAG<br>Lys | CAA<br>Gln<br>20 | TCC<br>Ser | CCG<br>Pro | CAG<br>Gln | 378 |
| GTG<br>Val | CTG<br>Leu<br>25 | CCG<br>Pro | GAG<br>Glu | GCC<br>Ala | AAC<br>Asn | GAG<br>Glu<br>30 | ACA<br>Thr | GAG<br>Glu | GCC<br>Ala | AGC<br>Ser | CCA<br>Pro<br>35 | GTG<br>Val | CAG<br>Gln | GCT<br>Ala | GAG<br>Glu | 426 |
| AAC<br>Asn<br>40 | GGG<br>Gly | TCT<br>Ser | CTG<br>Leu | GCC<br>Ala | TCA<br>Ser<br>45 | CTG<br>Leu | CGG<br>Arg | CAG<br>Gln | CTG<br>Leu | GAC<br>Asp<br>50 | ACA<br>Thr | GCC<br>Ala | TTC<br>Phe | TCA<br>Ser | CAG<br>Gln<br>55 | 474 |
| CTG<br>Leu | AGG<br>Arg | ACG<br>Thr | CGG<br>Arg | CTG<br>Leu<br>60 | CGC<br>Arg | AAC<br>Asn | GTC<br>Val | ACC<br>Thr | TTG<br>Leu<br>65 | CAG<br>Gln | TTG<br>Leu | GCT<br>Ala | GGG<br>Gly | GAG<br>Glu<br>70 | CTG<br>Leu | 522 |
| GGC<br>Gly | ATA<br>Ile | GCA<br>Ala | GCC<br>Ala<br>75 | CCA<br>Pro | GAG<br>Glu | CCG<br>Pro | CGG<br>Arg | CGG<br>Arg<br>80 | CAT<br>His | GTC<br>Val | CTG<br>Leu | CTG<br>Leu | ATG<br>Met<br>85 | GCC<br>Ala | ACC<br>Thr | 570 |
| ACA<br>Thr | CGC<br>Arg | ACC<br>Thr<br>90 | GGC<br>Gly | TCC<br>Ser | TCC<br>Ser | TTC<br>Phe | GTT<br>Val<br>95 | GGG<br>Gly | GAG<br>Glu | TTC<br>Phe | TTC<br>Phe | AAC<br>Asn<br>100 | CAG<br>Gln | CAG<br>Gln | GGC<br>Gly | 618 |
| AAC<br>Asn | ATA<br>Ile<br>105 | TTC<br>Phe | TAC<br>Tyr | CTC<br>Leu | TTT<br>Phe | GAG<br>Glu<br>110 | CCC<br>Pro | CTG<br>Leu | TGG<br>Trp | CAC<br>His | ATC<br>Ile<br>115 | GAG<br>Glu | AGG<br>Arg | ACG<br>Thr | GTC<br>Val | 666 |
| ACT<br>Thr<br>120 | TTT<br>Phe | GAG<br>Glu | CCA<br>Pro | GGG<br>Gly | GGG<br>Gly<br>125 | GCC<br>Ala | AAC<br>Asn | GCG<br>Ala | GTG<br>Val | GGC<br>Gly<br>130 | TCG<br>Ser | GCC<br>Ala | CTG<br>Leu | GTG<br>Val | TAC<br>Tyr<br>135 | 714 |
| CGC<br>Arg | GAC<br>Asp | GTG<br>Val | CTG<br>Leu | CAG<br>Gln<br>140 | CAG<br>Gln | CTC<br>Leu | CTC<br>Leu | CTC<br>Leu | TGC<br>Cys<br>145 | GAC<br>Asp | CTC<br>Leu | TAC<br>Tyr | ATT<br>Ile | CTG<br>Leu<br>150 | GAG<br>Glu | 762 |
| AGC<br>Ser | TTC<br>Phe | ATC<br>Ile | TCA<br>Ser<br>155 | CCA<br>Pro | GCG<br>Ala | CCC<br>Pro | GAG<br>Glu | GAG<br>Glu<br>160 | CAC<br>His | CTA<br>Leu | ACT<br>Thr | GCT<br>Ala | GCC<br>Ala<br>165 | CTG<br>Leu | TTC<br>Phe | 810 |
| CGG<br>Arg | CGG<br>Arg | GGC<br>Gly<br>170 | TCC<br>Ser | AGC<br>Ser | CAC<br>His | TCA<br>Ser | CTC<br>Leu<br>175 | TGT<br>Cys | GAG<br>Glu | GAG<br>Glu | CCC<br>Pro | GTC<br>Val<br>180 | TGC<br>Cys | ACA<br>Thr | CCC<br>Pro | 858 |
| AGC<br>Ser | CTC<br>Leu<br>185 | AAG<br>Lys | AAG<br>Lys | GTC<br>Val | TTT<br>Phe | GAG<br>Glu<br>190 | AAG<br>Lys | TAC<br>Tyr | CAC<br>His | TGC<br>Cys | AAG<br>Lys<br>195 | AAC<br>Asn | CGC<br>Arg | CGC<br>Arg | TGC<br>Cys | 906 |
| GGG<br>Gly<br>200 | CCT<br>Pro | CTC<br>Leu | AAC<br>Asn | ATC<br>Ile | ACG<br>Thr<br>205 | CTG<br>Leu | GCA<br>Ala | GCT<br>Ala | GAA<br>Glu | GCA<br>Ala<br>210 | TGC<br>Cys | CGG<br>Arg | CGC<br>Arg | AAG<br>Lys | CAG<br>Gln<br>215 | 954 |
| CAC<br>His | ATG<br>Met | GCC<br>Ala | TTG<br>Leu | AAG<br>Lys<br>220 | ACG<br>Thr | GTG<br>Val | CGC<br>Arg | ATC<br>Ile | CGG<br>Arg<br>225 | CAG<br>Gln | CTG<br>Leu | GAG<br>Glu | TTC<br>Phe | CTG<br>Leu<br>230 | CAG<br>Gln | 1002 |
| CCC<br>Pro | CTG<br>Leu | GCC<br>Ala | GAG<br>Glu | GAC<br>Asp<br>235 | CCG<br>Pro | CGG<br>Arg | CTG<br>Leu | GAC<br>Asp<br>240 | CTG<br>Leu | CGC<br>Arg | ATT<br>Ile | ATC<br>Ile | CAG<br>Gln<br>245 | CTG<br>Leu | GTG<br>Val | 1050 |
| CGG<br>Arg | GAC<br>Asp | CCA<br>Pro<br>250 | CGT<br>Arg | GCC<br>Ala | GTG<br>Val | CTG<br>Leu | GTG<br>Val<br>255 | TCG<br>Ser | CGC<br>Arg | ATG<br>Met | GTG<br>Val | GCC<br>Ala<br>260 | TTC<br>Phe | TCG<br>Ser | GGC<br>Gly | 1098 |
| AAG<br>Lys | TAC<br>Tyr<br>265 | GAG<br>Glu | AGC<br>Ser | TGG<br>Trp | AAG<br>Lys | AAG<br>Lys<br>270 | TGG<br>Trp | GCG<br>Ala | GCC<br>Ala | GAG<br>Glu | GGG<br>Gly<br>275 | GAG<br>Glu | GCC<br>Ala | CCG<br>Pro | CTG<br>Leu | 1146 |

| | | | | | | | | | | | | | | | | |
|---|---|---|---|---|---|---|---|---|---|---|---|---|---|---|---|---|
| CAG | GAG | GAC | GAG | GTG | CAA | CGG | CTG | CGG | GGC | AAC | TGC | GAG | AGC | ATC | CGG | 1194 |
| Gln | Glu | Asp | Glu | Val | Gln | Arg | Leu | Arg | Gly | Asn | Cys | Glu | Ser | Ile | Arg | |
| 280 | | | | | 285 | | | | 290 | | | | | | 295 | |
| CTG | TCG | GCC | GAG | CTG | GGA | CTG | CGG | CAG | CCG | CGC | TGG | CTG | CGA | GGC | CGT | 1242 |
| Leu | Ser | Ala | Glu | Leu | Gly | Leu | Arg | Gln | Pro | Arg | Trp | Leu | Arg | Gly | Arg | |
| | | | | 300 | | | | 305 | | | | | 310 | | | |
| TAC | ATG | CTG | GTG | CGC | TAC | GAG | GAC | GTG | GCA | CGG | GCG | CCG | CTG | CGC | AAG | 1290 |
| Tyr | Met | Leu | Val | Arg | Tyr | Glu | Asp | Val | Ala | Arg | Ala | Pro | Leu | Arg | Lys | |
| | | | 315 | | | | | 320 | | | | | 325 | | | |
| GCG | CTG | GAG | ATG | TAC | CGC | TTC | GCC | GGC | ATC | CAC | CCC | ACG | CCA | CAG | GTG | 1338 |
| Ala | Leu | Glu | Met | Tyr | Arg | Phe | Ala | Gly | Ile | His | Pro | Thr | Pro | Gln | Val | |
| | | 330 | | | | | 335 | | | | | 340 | | | | |
| GAG | GAG | TGG | ATC | CGC | GCC | AAC | ACG | CAG | GCA | CCA | CAG | GAC | AGC | AAC | GGC | 1386 |
| Glu | Glu | Trp | Ile | Arg | Ala | Asn | Thr | Gln | Ala | Pro | Gln | Asp | Ser | Asn | Gly | |
| | 345 | | | | | 350 | | | | | 355 | | | | | |
| ATT | TAC | TCC | ACG | CAG | AAG | AAC | TCC | TCG | GAG | CAG | TTT | GAG | AAG | TGG | CGG | 1434 |
| Ile | Tyr | Ser | Thr | Gln | Lys | Asn | Ser | Ser | Glu | Gln | Phe | Glu | Lys | Trp | Arg | |
| 360 | | | | | 365 | | | | | 370 | | | | | 375 | |
| TTC | AGC | ATC | CCC | TTC | AAG | CTG | GCG | CAG | GTG | GTG | CAG | GAC | GCC | TGC | GAG | 1482 |
| Phe | Ser | Ile | Pro | Phe | Lys | Leu | Ala | Gln | Val | Val | Gln | Asp | Ala | Cys | Glu | |
| | | | | 380 | | | | 385 | | | | | | 390 | | |
| CCA | GCC | ATG | AGG | CTC | TTT | GGC | TAC | AAG | CTG | GCC | AGC | AGT | GCC | CAG | GAG | 1530 |
| Pro | Ala | Met | Arg | Leu | Phe | Gly | Tyr | Lys | Leu | Ala | Ser | Ser | Ala | Gln | Glu | |
| | | | 395 | | | | | 400 | | | | | 405 | | | |
| CTG | ACC | AAC | CGC | TCG | CTC | AGC | CTG | CTG | GAG | GAG | GGG | CCC | CCC | ACA | CGG | 1578 |
| Leu | Thr | Asn | Arg | Ser | Leu | Ser | Leu | Leu | Glu | Glu | Gly | Pro | Pro | Thr | Arg | |
| | | 410 | | | | | 415 | | | | | 420 | | | | |
| ATC | ACG | TAGTGTGGCA | | CCGCTGCCCC | | CGTATGCCCG | | GCCGGCCCGA | | GGTGACCCTG | | | | | | 1634 |
| Ile | Thr | | | | | | | | | | | | | | | |
| | 425 | | | | | | | | | | | | | | | |

| | | | | | |
|---|---|---|---|---|---|
| TGCCATGGAC | TAGGAACCGG | GGTGTCCTCG | CAATAGCGAT | GGGTTCTTGG | GAAGGGCGAT | 1694 |
| CAGGAGATGG | CACAGGGATG | CTGCGGCAGA | GGGGTGAAGC | TGTTTAGTTC | CTCTCCCGAT | 1754 |
| GGAAGGATGA | GACCCTGCGA | TTGAAAACCC | AAGCACAGTG | GGTGCCCAGA | GCCCTGAGCA | 1814 |
| CAACCTGACC | CGTGTGCCAG | CTCCAGCGGT | GCCTTCTCAT | TTCTGCAGAG | GGCCATTGAG | 1874 |
| CGAAGCACAG | GAGAACTGGA | ATTTGCAGCC | AGGAATCCAT | AGCCACAACC | AGGGGACAAT | 1934 |
| TTACTGGGAG | TGTTCAGCGA | TCTGGAGGTT | TTCCAGTGCC | ACCAAACACA | ATGAGCACTC | 1994 |
| CTGGGTGGAC | TCCAGCACGG | GAAGCAGTGT | CGTTGCCCCA | TGGGCACATG | CTCTCTGCGT | 2054 |
| TTTCCAGTGT | TGTGCAACGA | GTGCCAGCAG | CATGGTGTGC | CAGCACCAGC | AGGGACTTCA | 2114 |
| ACCTCAAAGG | CCTTCTGGTT | TAGTGCCTTG | GTACCAGCAC | AGACTGGGAG | CTGCCTGCAG | 2174 |
| CAGGACGAGG | CGGCCCCTCA | GTTATTGCTC | TGCAGTGCTG | ATTGTTGGGT | GTGTGGGGGG | 2234 |
| GTCCTTTTGA | TTTATTTTCT | ACATTTTTCT | CTGTGTACCG | GGGTTGTGGA | GCAAATTTAT | 2294 |
| TTATTTATTA | TGTTTAAAAC | AACAAAGGCA | AGGAGGGGG | TGGGGGAAG | ATACATCAGG | 2354 |

( 2 ) INFORMATION FOR SEQ ID NO:2:

( i ) SEQUENCE CHARACTERISTICS:
        ( A ) LENGTH: 458
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Glu | Arg | Arg | Ser | Ala | Leu | Pro | Gln | Asp | Phe | Arg | Glu | Val | Leu | His |
| -33 | | | -30 | | | | | -25 | | | | | -20 | | |
| Cys | Leu | Lys | Met | Arg | Ser | Lys | Tyr | Ala | Val | Leu | Leu | Val | Phe | Val | Val |

-continued

|     |     |     |     | -15 |     |     |     |     | -10 |     |     |     |     | -5  |
| --- | --- | --- | --- | --- | --- | --- | --- | --- | --- | --- | --- | --- | --- | --- |

Gly Leu Val Ile Ile Glu Lys Glu Asn Asn Phe Ile Ser Arg Val Ser
        1               5                   10                  15

Asp Lys Leu Lys Gln Ser Pro Gln Val Leu Pro Glu Ala Asn Glu Thr
                    20              25              30

Glu Ala Ser Pro Val Gln Ala Glu Asn Gly Ser Leu Ala Ser Leu Arg
                35              40                  45

Gln Leu Asp Thr Ala Phe Ser Gln Leu Arg Thr Arg Leu Arg Asn Val
            50              55              60

Thr Leu Gln Leu Ala Gly Glu Leu Gly Ile Ala Ala Pro Glu Pro Arg
        65                  70              75

Arg His Val Leu Leu Met Ala Thr Thr Arg Thr Gly Ser Ser Phe Val
80                      85              90                  95

Gly Glu Phe Phe Asn Gln Gln Gly Asn Ile Phe Tyr Leu Phe Glu Pro
                100             105                 110

Leu Trp His Ile Glu Arg Thr Val Thr Phe Glu Pro Gly Gly Ala Asn
            115             120             125

Ala Val Gly Ser Ala Leu Val Tyr Arg Asp Val Leu Gln Gln Leu Leu
        130             135             140

Leu Cys Asp Leu Tyr Ile Leu Glu Ser Phe Ile Ser Pro Ala Pro Glu
    145             150             155

Glu His Leu Thr Ala Ala Leu Phe Arg Arg Gly Ser Ser His Ser Leu
160             165             170             175

Cys Glu Glu Pro Val Cys Thr Pro Ser Leu Lys Lys Val Phe Glu Lys
                180             185             190

Tyr His Cys Lys Asn Arg Arg Cys Gly Pro Leu Asn Ile Thr Leu Ala
            195             200             205

Ala Glu Ala Cys Arg Arg Lys Gln His Met Ala Leu Lys Thr Val Arg
        210             215             220

Ile Arg Gln Leu Glu Phe Leu Gln Pro Leu Ala Glu Asp Pro Arg Leu
    225             230             235

Asp Leu Arg Ile Ile Gln Leu Val Arg Asp Pro Arg Ala Val Leu Val
240             245             250             255

Ser Arg Met Val Ala Phe Ser Gly Lys Tyr Glu Ser Trp Lys Lys Trp
                260             265             270

Ala Ala Glu Gly Glu Ala Pro Leu Gln Glu Asp Glu Val Gln Arg Leu
            275             280             285

Arg Gly Asn Cys Glu Ser Ile Arg Leu Ser Ala Glu Leu Gly Leu Arg
        290             295             300

Gln Pro Arg Trp Leu Arg Gly Arg Tyr Met Leu Val Arg Tyr Glu Asp
    305             310             315

Val Ala Arg Ala Pro Leu Arg Lys Ala Leu Glu Met Tyr Arg Phe Ala
320             325             330             335

Gly Ile His Pro Thr Pro Gln Val Glu Glu Trp Ile Arg Ala Asn Thr
                340             345             350

Gln Ala Pro Gln Asp Ser Asn Gly Ile Tyr Ser Thr Gln Lys Asn Ser
            355             360             365

Ser Glu Gln Phe Glu Lys Trp Arg Phe Ser Ile Pro Phe Lys Leu Ala
        370             375             380

Gln Val Val Gln Asp Ala Cys Glu Pro Ala Met Arg Leu Phe Gly Tyr
    385             390             395

Lys Leu Ala Ser Ser Ala Gln Glu Leu Thr Asn Arg Ser Leu Ser Leu
400             405             410             415

```
Leu Glu Glu Gly Pro Pro Thr Arg Ile Thr
            420                 425
```

(2) INFORMATION FOR SEQ ID NO:3:

(i) SEQUENCE CHARACTERISTICS:
        (A) LENGTH: 14
        (B) TYPE: amino acid
        (D) TOPOLOGY: linear (ii) MOLECULE TYPE: peptide (xi) SEQUENCE DESCRIPTION: SEQ ID NO:3:

```
Leu Val Ile Xaa Xaa Xaa Xaa Asn Asn Phe Ile Xaa Xaa Val
1                5                   10
```

(2) INFORMATION FOR SEQ ID NO:4:

(i) SEQUENCE CHARACTERISTICS:
        (A) LENGTH: 14
        (B) TYPE: amino acid
        (D) TOPOLOGY: linear (ii) MOLECULE TYPE: peptide (xi) SEQUENCE DESCRIPTION: SEQ ID NO:4:

```
Xaa Val Ile Xaa Glu Xaa Xaa Asn Asn Phe Ile Xaa Xaa Val
1                5                   10
```

(2) INFORMATION FOR SEQ ID NO:5:

(i) SEQUENCE CHARACTERISTICS:
        (A) LENGTH: 24
        (B) TYPE: amino acid
        (D) TOPOLOGY: linear (ii) MOLECULE TYPE: peptide (xi) SEQUENCE DESCRIPTION: SEQ ID NO:5:

```
Leu Val Ile Xaa Glu Lys Glu Asn Asn Phe Ile Ser Arg Val Ser Asp
1                5                   10                  15
Lys Leu Lys Xaa Xaa Pro Xaa Val
            20
```

(2) INFORMATION FOR SEQ ID NO:6:

(i) SEQUENCE CHARACTERISTICS:
        (A) LENGTH: 13
        (B) TYPE: amino acid
        (D) TOPOLOGY: linear (ii) MOLECULE TYPE: peptide (xi) SEQUENCE DESCRIPTION: SEQ ID NO:6:

```
Ser Phe Ile Ser Pro Ala Pro Glu Glu Xaa Leu Thr Ala
1                5                   10
```

(2) INFORMATION FOR SEQ ID NO:7:

(i) SEQUENCE CHARACTERISTICS:
        (A) LENGTH: 28
        (B) TYPE: nucleic acid
        (C) STRANDEDNESS: single
        (D) TOPOLOGY: linear (ii) MOLECULE TYPE: Other nucleic acid..synthetic DNA (xi) SEQUENCE DESCRIPTION: SEQ ID NO:7:

```
CAAAGCTTGA RAARGARAAY AAYTTYAT                                  28
```

(2) INFORMATION FOR SEQ ID NO:8:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: Other nucleic acid..synthetic DNA (xi) SEQUENCE DESCRIPTION: SEQ ID NO:8:

MGKGTKWSKG AYAARCTNAA                                      20

(2) INFORMATION FOR SEQ ID NO:9:

(i) SEQUENCE CHARACTERISTICS:
        (A) LENGTH: 29
        (B) TYPE: nucleic acid
        (C) STRANDEDNESS: single
        (D) TOPOLOGY: linear (ii) MOLECULE TYPE: Other nucleic acid..synthetic DNA (xi) SEQUENCE DESCRIPTION: SEQ ID NO:9:

AARTADWSKG GKCGKGGKCT TCTTAAGCT                         29